United States Patent
Roche et al.

(10) Patent No.: US 9,913,725 B2
(45) Date of Patent: *Mar. 13, 2018

(54) SYSTEM AND METHOD FOR PERFORMING PERCUTANEOUS SPINAL INTERBODY FUSION

(71) Applicant: Spineology, Inc., St. Paul, MN (US)

(72) Inventors: Karen Roche, Stillwater Township, MN (US); Clint Boylan, Minneapolis, MN (US); Dan McPhillips, Ham Lake, MN (US); Tim Walnofer, Stillwater, MN (US); Joseph Gleason, Eagan, MN (US)

(73) Assignee: Spineology, Inc., St. Paul, MN (US)

( * ) Notice: Subject to any disclaimer, the term of this patent is extended or adjusted under 35 U.S.C. 154(b) by 50 days.

This patent is subject to a terminal disclaimer.

(21) Appl. No.: 15/207,430

(22) Filed: Jul. 11, 2016

(65) Prior Publication Data

US 2017/0007417 A1 Jan. 12, 2017

Related U.S. Application Data

(63) Continuation of application No. 14/563,987, filed on Dec. 8, 2014, now Pat. No. 9,387,088, which is a continuation of application No. 12/650,889, filed on Dec. 31, 2009, now Pat. No. 8,906,094.

(60) Provisional application No. 61/141,985, filed on Dec. 31, 2008.

(51) Int. Cl.
*A61F 2/44* (2006.01)
*A61B 17/70* (2006.01)
*A61B 17/16* (2006.01)
*A61B 17/34* (2006.01)

(52) U.S. Cl.
CPC .......... *A61F 2/441* (2013.01); *A61B 17/1671* (2013.01); *A61B 17/7097* (2013.01); *A61F 2/4455* (2013.01); *A61B 17/1617* (2013.01); *A61B 17/3423* (2013.01)

(58) Field of Classification Search
CPC ........................... A61F 2/441; A61B 17/1671
See application file for complete search history.

(56) References Cited

U.S. PATENT DOCUMENTS

| | | | | |
|---|---|---|---|---|
| 3,875,595 | A * | 4/1975 | Froning | A61F 2/441 623/17.12 |
| 4,759,769 | A * | 7/1988 | Hedman | A61F 2/4425 623/17.13 |
| 5,549,679 | A * | 8/1996 | Kuslich | A61B 17/7098 606/247 |
| 2005/0043808 | A1 * | 2/2005 | Felt | A61B 17/1739 623/20.14 |

* cited by examiner

*Primary Examiner* — Christian Sevilla
(74) *Attorney, Agent, or Firm* — Skaar Ulbrich Macari, P.A.

(57) ABSTRACT

A method of performing percutaneous interbody spinal fusion on adjacent vertebrae in a patient including the steps of: creating a percutaneous access opening on the patient, using indirect visualization to establish a surgical path through the access opening via neural monitoring, creating a cavity in a disc space between the adjacent vertebra, without retraction, evaluating the created cavity, inserting a container sized and configured to fit through the access opening into the cavity and filling the container with fill material.

20 Claims, 20 Drawing Sheets

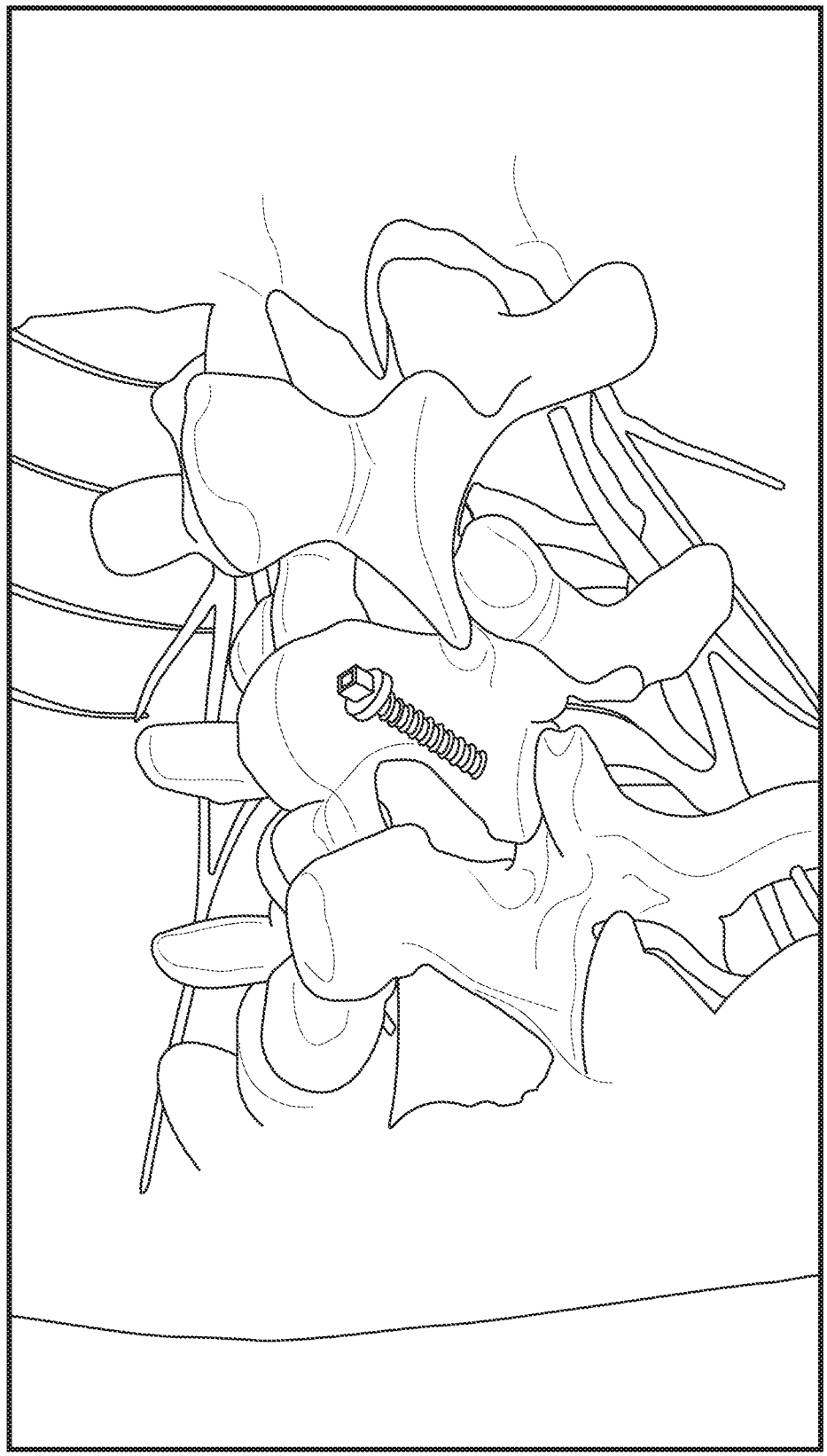

SYSTEM AND METHOD FOR PERFORMING PERCUTANEOUS SPINAL INTERBODY FUSION

PRIORITY

The present application is a continuation of U.S. patent application Ser. No. 14/563,987, filed Dec. 8, 2014, now U.S. Pat. No. 9,387,088, which is a continuation of U.S. patent application Ser. No. 12/650,889, filed Dec. 31, 2009, now U.S. Pat. No. 8,906,094, which claims the benefit of U.S. Provisional Application No. 61/141,985, filed Dec. 31, 2008. Each of the foregoing applications is herein incorporated by reference in their entirety.

FIELD

The present invention relates generally to a system and method for performing a spinal interbody fusion. In particular, the present invention relates to a system and method for performing percutaneous spinal interbody fusion.

BACKGROUND

It is recognized that the spinal disc consists of three parts: first, the nucleus, a central portion that is a compression-resisting cushion; second, the annulus, a peripheral rim portion that is a tension-resisting hoop; and third, the end plates, the superior and inferior borders of the disc, consisting of the upper and lower surfaces of the vertebral body bones adjacent to the disc. Many studies have concluded that mechanical back pain is the most common and costly musculoskeletal condition affecting middle-aged humans in modern societies. Mechanical back pain may be caused by several factors, but overwhelming evidence suggests that degeneration of the spinal intervertebral disc, such as may be caused by Degenerative Disc Disease (DDD) is the most common condition causing back pain symptoms.

Many devices have been invented for the purpose of stabilizing and/or replacing parts of the disc in an effort to ease the pain associated with degenerative disc disease. Previous devices designed to treat DDD fall generally into the following four classes:

The first class includes rigid, three-dimensional geometric solid devices, either impervious or porous, that function as support struts. When these devices are placed between adjacent vertebral bodies they allow, and in some cases encourage bone to grow through and/or around the device to cause a bony fusion between two adjacent vertebral bodies. Rigid implants fabricated from metal, ceramic, or hard plastics suffer from several disadvantages such as: the need to create large surgical exposures disruptive to muscle and soft tissue, the need for large destabilizing entrance holes through the annulus of the disc, and the presence of large volumes of non-biologic material that reduce bone graft surface contact at the end plate.

The second class involves the use of semi-rigid artificial joints that allow motion in one or more planes. Examples include: U.S. Pat. No. 4,759,769 to Kostuik; U.S. Pat. No. 6,039,763 to Shelokov, and commercially available examples such as the Link device or the Charite Intervertebral Disc Endoprosthesis. These artificial joints have several disadvantages, including: the artificial joints are technically challenging to the surgeon in that proper placement of the device can be quite difficult, placement of the device requires large anterior exposures and re-operation procedures, if needed, are dangerous (life-threatening) due to anterior scarring and inability to use another surgical approach.

The third class is directed to non-rigid cushions designed to replace the nucleus of the disc. Examples of artificial discs are described in U.S. Pat. No. 4,904,260 to Ray, U.S. Pat. No. 4,772,287 to Ray and U.S. Pat. No. 5,192,326 to Bao. These devices are prone to wear and subsidence and as such pose a risk to the surrounding anatomy when they become dislocated out of the disc space.

Finally, the fourth class is the relatively new area of initially flexible, deployable containers that become rigid when injected with materials that can support loads. Examples include U.S. Pat. Nos. 5,571,189, 5,549,679 and 6,712,853 to Kuslich, the contents of which are incorporated in the entirety herein, each of which describe deployable, porous containers, useful in stabilizing a deteriorating spinal disc. The container is placed into a reamed out intervertebral space and is expanded by the introduction of graft material which may be tightly compacted within the container.

Like many other areas of surgery, spine surgery has become less invasive as smaller, more precise technology develops. Many minimally invasive intervertebral fusion devices exist, such as those disclosed in U.S. Pat. Nos. 5,571,189 and 5,549,679 and the commercially available XLIF® procedure by NuVasive. However, all minimally invasive fusion devices still require a surgical access opening that is as large as the device to be implanted. Generally speaking, the access aperture in minimally invasive procedures is at least 15-30 mm in diameter. Also, because minimally invasive procedures require direct visualization, the surgeon may need to cut bone and must significantly retract soft tissues and the nerve root, potentially causing nerve root injury or persistent post-operative pain.

By contrast, percutaneous surgery is done using x-ray visualization and image guidance and as such does not require resection of bony or soft tissue for direct visualization of the disc. Further, the incision is generally in the range of about 10 mm, much smaller than the access aperture in MIS procedures. Thus, percutaneous surgery results in a dramatic reduction in morbidity rates and more rapid recovery, both of which leading to significantly shorter hospitalization times.

U.S. Pat. Nos. 6,558,383 and 7,087,058 to Cragg describe a percutaneous method of fusing the lumbo-sacral region of the spine from an axial approach. The method and system described by Cragg are limited to fusing either the L5-S1 or the L4-L5-S1 motion segments using a rigid device and are further limited to an axial approach. Further, although Cragg describes the method as being percutaneous, the method still requires an access opening of at least 22 mm to accommodate the implant. The larger a surgical exposure is, the greater the likelihood of attendant bleeding and injury to local muscular, ligamentous, vascular and nervous tissues and in the lumbar region, the bowels may also be damaged.

Any device that would more easily, and/or more effectively, and/or more safely treat degenerative disc disease would be useful in the management of hundreds of thousands of suffering individuals. The current invention is an improvement to current systems and methods of performing interbody fusion because it enables surgeons to finally perform a true percutaneous interbody fusion at all levels of the spine.

The entire content of each and all patents, patent applications, articles and additional references, mentioned herein, are respectively incorporated herein by reference.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY

The system and method of the present invention accomplish true percutaneous interbody fusion. Unlike currently available systems, the present invention utilizes indirect x-ray visualization. According to one embodiment of the present invention, a posterolateral approach is used to access the spine. Using the percutaneous system and method of the present invention requires no nerve root, aorta, vena cava or dura retraction, there is no need to flip the patient over and there is very minimal bony resection. Thus, the percutaneous system and method of the present invention results in significantly less soft tissue damage, blood loss, post-operative pain, scar tissue and vascular injury than minimally invasive interbody fusion.

According to another aspect of the percutaneous system and method of the present invention, indirect, image guided visualization is used to accomplish interbody fusion at any location in the entire lumbar spine.

In an embodiment of the percutaneous system and method of the present invention the deployable container may conform to the size and shape of the endplates. According to one aspect, the deployable container may be inserted in a collapsed state through a percutaneous incision and filled with fill material to a size and shape significantly larger than the percutaneous access opening. This method of filling allows for distraction of the interbody space such that as the container is filled with fill material the motion segment may be lifted. In turn, this disc space distraction leads to indirect decompression of the nerve roots passing through the foramen at the affected level, helping to relieve the radicular leg pain commonly associated with degenerative disc disease.

According to another embodiment of the percutaneous system and method of the present invention, a neural stimulating component may be utilized to ensure a safe access trajectory for introduction of subsequent instruments to the surgical site. In one aspect, such neural stimulating component may have a diameter in the range of about 2 mm.

In one embodiment the present invention may be a method of performing percutaneous interbody spinal fusion on adjacent vertebrae of a patient that may include the steps of: creating an access opening on the patient, the access opening being less than 10 mm wide, using indirect visualization: establishing a surgical path through the access opening via neural monitoring, creating a cavity in a disc space of the adjacent vertebrae, evaluating the created cavity, inserting a container sized and configured to fit through the less than 10 mm access opening into the cavity and filling the container with fill material. According to one aspect of the present invention the method may further include the step of sequential dilation.

According to another aspect of the present invention, the method may further include the step of filling the container sufficiently to distract adjacent vertebrae.

In another embodiment, the present invention may be a system for performing percutaneous interbody spinal fusion on adjacent vertebrae of a patient that may include: imaging equipment adapted to provide indirect visualization of the patient, a neural stimulating component configured to establish a surgical path through a less than 10 mm access opening, at least one cavity creation tool, a discectomy evaluation device, a container sized and configured to fit through a less than 10 mm access opening and fill material adapted for filling the container.

According to one aspect of the present invention, the system may further include sequential dilators.

In yet another embodiment, the present invention may be a kit for performing percutaneous interbody spinal fusion on adjacent vertebrae of a patient which may include: imaging equipment adapted to provide indirect visualization of the patient, a neural stimulating component configured to establish a surgical path through a less than 10 mm access opening, at least one cavity creation tool, a discectomy evaluation device, a container sized and configured to fit through a less than 10 mm access opening, fill material adapted for filling the container and instructions for using the kit.

According to one aspect of the present invention, the kit may further include sequential dilators.

In another embodiment, the present invention may be a method for performing percutaneous interbody spinal fusion on adjacent vertebrae of a patient including the steps of: providing: imaging equipment adapted to provide indirect visualization of the patient, a neural stimulating component configured to establish a surgical path through a less than 10 mm access opening, at least one cavity creation tool, a discectomy evaluation device, a container sized and configured to fit through a less than 10 mm access opening, fill material adapted for filling the container and providing instructions for use.

BRIEF DESCRIPTION OF THE DRAWINGS

FIG. 20 illustrates screw placement according to an embodiment of the present invention.

DETAILED DESCRIPTION

Figure 1:
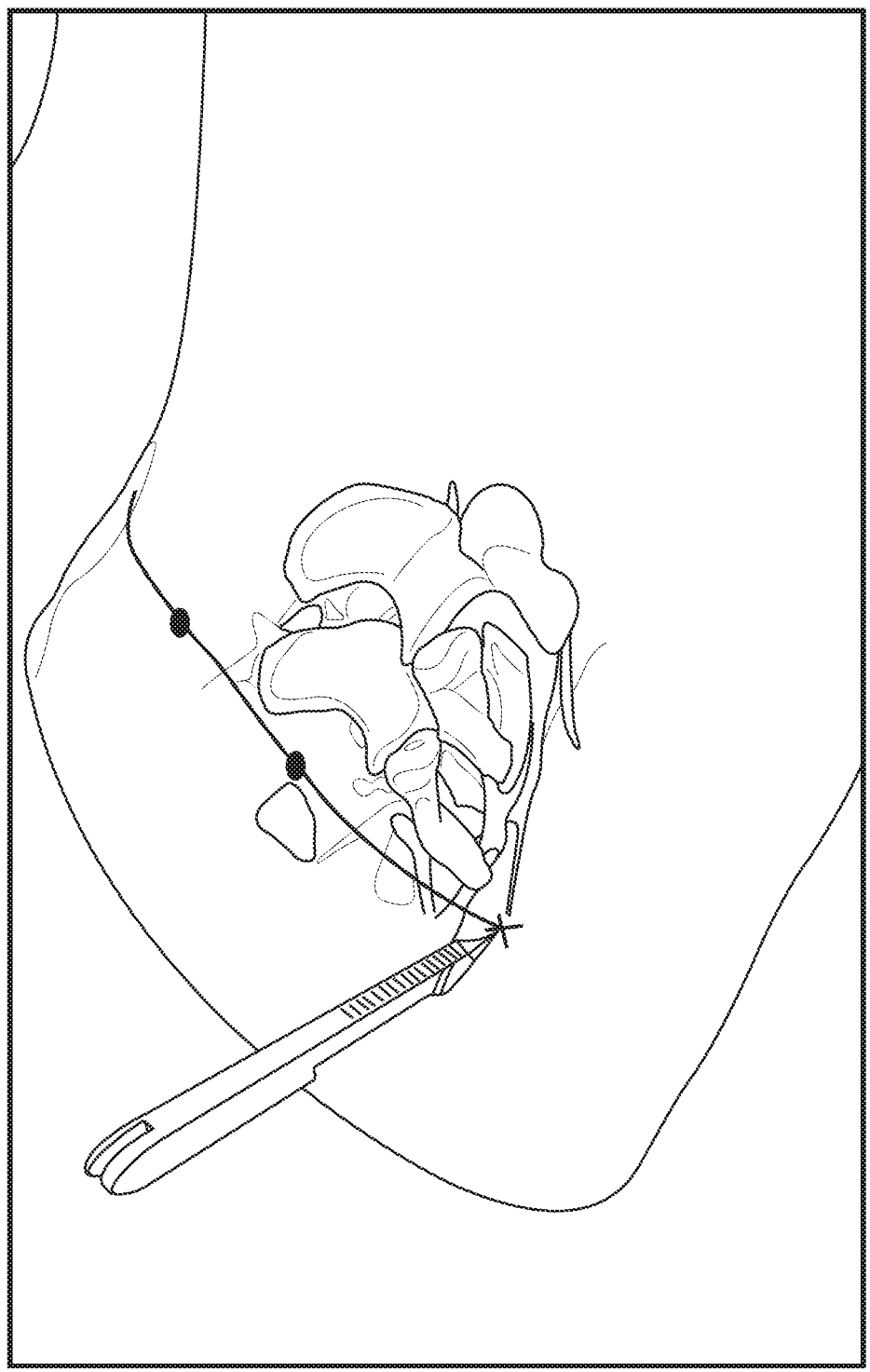
FIG. 1 illustrates an example percutaneous skin incision.

The present invention includes a comprehensive system and method for performing a true percutaneous interbody fusion. Generally, as shown in FIG. 1, the percutaneous incision is a small stab wound, no more than 10 mm in length. The system may include: a neural stimulating component, a discectomy evaluating device, disc removal/cavity creation tool(s), a deployable container and fill material. The steps of the method of present invention may include: using indirect visualization, percutaneously placing a neural stimulating component; preparing a fusion bed by creating a cavity; evaluating the cavity; inserting a container and filling the container with fill material.

According to the present invention, percutaneous interbody fusion is performed under indirect visualization using x-ray or other imaging visualization without any direct visualization. Because neural tissue cannot be seen on x-ray, there is a need for active neural monitoring to ensure there is no injury to the surrounding nerves during the procedure. There are two types of monitoring that are generally used in spine surgery: Electromyography (EMG) and Somatosenory Evoked Potential (SEP). When using neural monitoring in the spine, the surgeon is evaluating nerve potential, that is, its ability to react, and checking for evoked responses. An instrument, such as a neural stimulating component, is used to mechanically manipulate or electrically stimulate the nerve in order to evoke a response. The main difference between EMG and SEP is that EMG looks at muscle responses and therefore is used for tracking nerve root response and SEP is used for dorsal column monitoring or spinal cord responses.

The present invention includes methods and devices for performing neural monitoring, i.e. nerve root mapping and also implant stimulation for the metallic stabilizing implants such as pedicle screws. In one embodiment, the neural stimulating component may be a fully insulated wire shaft with an exposed blunt distal end portion. The insulated wire shaft may include a detachable handle and shaft that is sized to fit through a 3 mm exchange tube. In another embodiment, the neural stimulating component may be a fully insulated blunt shaft having an exposed distal end and detachable handle that is further sheathed with a cannula. In an alternate embodiment, the neural stimulating component may be an insulated guide pin with a fully shielded blunt tip having an exposed distal end and detachable handle that will accept a series of interim dilators that can be impacted, with a small cap, into the disc prior to an access portal. In yet another embodiment, any of the aforementioned neural stimulating components may include a sharp tip such that the tip could be used to pierce the disc following docking.

Figure 2:
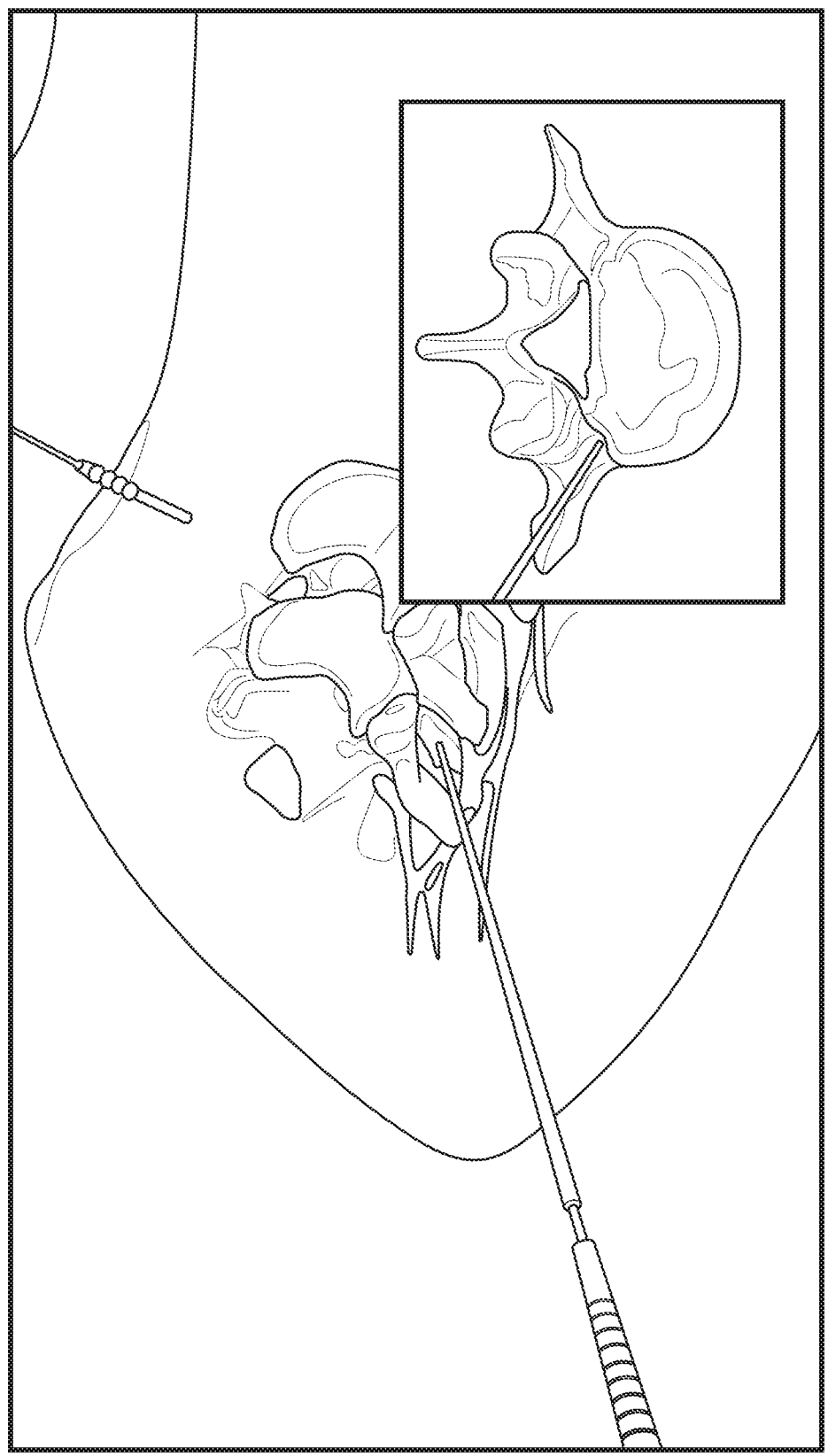
FIG. 2 depicts an example neural stimulating component inserted into a patient's anatomy.

In a preferred embodiment, as shown in FIG. 2, the neural stimulating component may be a fully insulated metal shaft with an affixed handle having a blunt tip with an exposed distal end. The neural stimulating component may have an exchange tube placed over the neural stimulating component. The exchange tube provides rigidity for neural stimulating component guidance through dense tissues and facilitates placement of sharps safely down to the spinal surface following identification of a safe trajectory by placement of the insulated probe. Inclusion of an exchange tube allows placement of sharps safely past the nerve root. In other words, inclusion of an exchange tube allows the delivery of a sharp cannulated spinal system pin or needle to the surface of the spine or into the spine. Such exchange tubes may be made of plastic or metal.

The exchange tube provides added rigidity to the neural stimulating component for ease of insertion. In the case of a metal exchange tube, the exchange tube is radiopaque for enhanced fluoroscopic monitoring. The exchange tube is shorter than the neural stimulating component to prevent electrical current from shunting to the tube rather than the being transferred to the tissue surrounding the tip. In use, the neural stimulating component is inserted with the exchange tube over the neural stimulating component tip but pulled back proximally against the neural stimulating component handle. The nerve root is safely traversed as confirmed by neuromonitoring, and the neural stimulating component tip may be seated against the outer surface of the annulus. The exchange tube may then be advanced over the neural stimulating component and docked at the annulus surface and the neural stimulating component may be removed, a standard guide pin may then be placed and the exchange tube may be removed. This embodiment and procedure permits safe navigation and placement of a cannula into the intervertebral disc for any subsequent type of intervertebral disc intervention or treatment.

Another embodiment may include a neural stimulating component that may be an insulated guide pin having a lead attached to its distal end. According to this embodiment, the monitoring technique may include passing the guide pin into the patient while the guide pin is electrified. If no response is evoked, the pin may then be tapped into the disc.

Any embodiment of the neural stimulating component may be pre-packed sterile and disposable for surgeon convenience.

Features of any embodiment of the neural stimulating component may include: a blunt tip to prevent the potential for nerve damage due to puncture and to ensure uniform electrical flow out of the tip; the component may be insulated to within ½ to 1 mm of the tip to concentrate stimulus location and to prevent electrical shunting to an exchange tube; an exposure in the range of about 0.5 mm at the neural stimulating component tip enables targeted delivery of the current to map neural structures and define a clear trajectory during percutaneous pin or needle placement in spinal procedures; the neural stimulating component can be used with most standard monitoring systems.

In another embodiment, the neural stimulating component may have a concentric bipolar design. In contrast to a monopolar design, the bipolar design includes an electrical return that is integrated into the component itself rather than being a separate pin that is placed in the patient as is done with monopolar designs.

The neural stimulating component may be in the range of about 150 to 200 mm in length and 1 to 2 mm in diameter. The exchange tube is in the range of about 125 to 175 mm in length with an inner diameter of about 2.5 mm and a very thin wall. In the event the exchange tube is comprised of plastic, the exchange tube length may equal the length of the neural stimulating component.

The present invention may also include a series of one or more soft tissue dilators for safe insertion of a larger working cannula to accommodate other surgical instruments. In order to mitigate any potential nerve root irritation a set of incremental dilators is envisioned. In one embodiment, the system and method of the present invention may include placing a guide pin in the range of about 2.5 mm through the exchange tube safely placed by use of a neural stimulating component as described above, then placing a dilator in the range of about 4 mm over the pin which opens the disc space and then a dilator in the range of about 6.5 mm may be placed over the about 4 mm dilator.

The preferred embodiment of each dilator includes a tapered tip for ease of insertion and for gentle deflection of the nerve roots or other soft tissue structures which the dilator passes. Each dilator size will have a corresponding impactor device in the form of a cap which passes freely over the previously passed pin or dilator to prevent inadvertent advancement, but which permits advancement of the dilator by impacting with a mallet if needed. The abovementioned sizes are for example only and one of ordinary skill in the art will recognize that variations in the sizes and the number of dilators used are within the scope of the disclosure.

The intent of the incremental dilators is to gradually increase the diameter from a guide pin diameter, typically in the range of about 1 to 2.5 mm, up to the desired access portal diameter, typically in the range of about 5.5 to 7.5 mm. The dilation step of the present invention includes penetrating the surface of the annulus to enter the disc space with the dilators and not merely placing the dilators on the surface of the spine.

The incremental dilation is gentler than conventional dilation techniques. By moving the superior vertebra in relation to the inferior vertebra via insertion of a first dilator, the nerve will move slightly as well and increase the peri-neural volume such that the next larger dilator can be more safely placed. By penetrating the disc surface with the dilators, any neural structures that are in close proximity to the dilator will be deflected out of the way until they are at the major diameter of the part. Then, when the next larger dilator is passed over the previously placed smaller dilator, the minor diameter of the larger dilator will be able to pass by the root and deflect the root further out of the way until the root is now at the major diameter of that larger dilator.

This incremental dilation with insertion of the tapered dilator tip into the disc space and the corresponding gradual deflection of the nerve root to the dilator's major diameter varies greatly from other tissue dilators that dock against the spine surface. With docking types of systems, the first dilator tip contacts the surface of the annulus but does not penetrate the intervertebral disc space. The next larger dilator then comes down to the disc surface and as the tapered tip of the larger dilator passes the tapered tip on the smaller dilator a gap is formed. This gap creates the potential for a nerve to become entrapped against the surface of the spine below the tip of the larger dilator.

The dilators of the present invention may be radiopaque, radiolucent or at least partially lucent. The benefit of the radiolucency is that it will make the impaction depth of an access portal seating over the dilator easier to view with an x-ray. This impaction depth is critical to ensuring good container size selection and optimal positioning. The dilators may be made of a plastic, aluminum or any other suitable materials and may be color coded for size.

The system of the present invention may also include a shaper to cut out the intervertebral space to create a cavity and prepare a fusion bed of bleeding bone at the endplates to facilitate new bone growth for fusion to occur. Any shaper that can be introduced percutaneously may be used. In some embodiments a tissue removal device, such as is disclosed in co-pending application Ser. No. 12/056,025 the disclosure of which is incorporated herein in its entirety, may also be used to evacuate the intervertebral cavity. In a preferred embodiment, a shaper as is disclosed in co-pending application Ser. No. 10/842,057, the disclosure of which is incorporated herein in its entirety, may be used.

Thorough preparation of the intervertebral disc space is also enhanced by the use of other tools adapted for percutaneous use, such as curettes, pituitary rongeurs, other surgical graspers, and suction/irrigation equipment. According to an embodiment the cavity created is larger than the access opening. In one embodiment of the present invention, an articulating curette may be used to create a cavity in a single plane, that is the width of the cavity may be created independent of the height of the cavity. The articulating motion also allows for the creation of a cavity off to one side of the disc space, if desired.

In one embodiment of the present invention, the shaping/cutting tools maybe set to different lengths and angles to determine the volume of disc material removed.

The system and method of the present invention may also include a discectomy evaluation component comprising a cannula having a bladder portion at its distal end. The discectomy evaluation device may be used to determine the thoroughness of the discectomy. In an embodiment, the bladder of the discectomy evaluation device may be compliant so that it will conform to the created cavity rather than cause the creation of a cavity. In one aspect, the bladder portion of the discectomy evaluating device may be comprised of latex, silicone, polyurethane or any other material that is compliant at low pressures. In an embodiment of the present invention, the cannula of the discectomy evaluating device may be comprised of PEBAX. In another embodiment, the discectomy evaluating device may be non-compliant, such that upon filling, the device will generate lift and terminate at a filled size that corresponds to the desired container size.

The discectomy evaluating device may be in the range of about 4 to 6 mm in diameter in its collapsed state for insertion through a cannula, and in the range of about 2.5 to 20 cc when inflated. In one embodiment, the assembly of the discectomy evaluation device may include small radiopaque marker bands for x-ray visualization of the position of the device upon its initial insertion.

The discectomy evaluating device may be placed on a radiopaque cannula so that it may be seen on x-ray upon insertion. In one embodiment, the discectomy evaluating device may be placed in a radiopaque protective insertion sheath to protect the bladder while remaining lucent.

In a preferred embodiment, the discectomy evaluating device may be placed on an internal cannula of sufficient diameter to allow the discectomy evaluating component to be inflated using low pressure with a simple syringe. With a smaller diameter and greater length, the cannula will require greater inflation and deflation force. Using high pressure could cause the undesirable extrusion of unretrieved disc nucleus material.

The discectomy evaluation device cannula dimensions may range from about 1 mm to 3 mm diameter and of sufficient length to pass through an access portal and enable the operator's hands to be outside of the x-ray beam. The bladder of the discectomy evaluation device may include an inverted tip which allows distal expansion past the cannula so that the entire cannula need not be inserted into the disc space.

In order to see the location and relative volume of the cavity that has been created in the disc space, the physician may inflate the discectomy evaluation device with radioopaque dye. This iterative step may help to identify incomplete removal of disc fragments and to guide the surgeon in further disc removal. In another embodiment the discectomy evaluation device material may be radio-opaque, or may include radio-opaque markers and then the discectomy evaluation component may be inflated with saline.

The discectomy evaluation device cannula may also include a valve to allow the surgeon to fill the discectomy evaluation component, close the valve to maintain the filled volume, and then step out of the radiation zone as the image is taken. In another embodiment, the discectomy evaluation component may identify annular defects and endplate fissures as it conforms to the cavity.

The system of the present invention may also include a porous container. The container is pliable and malleable before its interior space is filled with fill material. The material of the container may be configured to take on the shape of the cavity in which the container is placed. The container may be sized, in the range from about 1 to about 4 cm in diameter, being roughly spherical or cylindrical in shape, although other ellipsoidal shapes and other geometric shapes may be used. In an initial collapsed condition, the container may be inserted into the created cavity through a very small opening in the range from about 3 mm to about 10 mm in diameter.

The container may be constructed from material that is woven, knitted, braided or form-molded to a density that will allow ingress and egress of fluids and solutions and will allow the ingrowth and through-growth of blood vessels and fibrous tissue and bony trabeculae to promote fusion, but the porosity may be tight enough to retain small particles of enclosed material, such as ground up bone graft, or bone graft substitute such as hydroxyapatite or other osteoconductive biocompatible materials known to promote bone formation. The container may include a plurality of pores. Generally, the pores may have a diameter of about 0.25 mm or less to about 5.0 mm. The size is selected to allow tissue ingrowth and bony fusion while containing the material packed into the container. If bone cement or other material is used which will not experience bone ingrowth, the pores may be much tighter to prevent egress of the media from within the container out into the cavity. This prevents leakage that could impinge upon nerves, blood vessels or the like if the fill material is allowed to exit the bone. When the container is fully filled with fill material, the container will form a self-retaining shape which conforms to and substantially fills the cavity.

The size and density of the pores determine the ease or difficulty with which materials may pass through the container. For instance, very small pores (<0.5 mm) would prohibit passage of all but the smallest particles and liquids. The pore size and density could be controlled in the manufacturing process, such that the final product would be matched to the needs of the surgeon. For example, if methylmethacrylate bone cement were to be used, the pore size would need to be very small, such as about less than 0.5 mm to about 1.0 mm, whereas, when bone graft or biocompatible ceramic granules are used, pore sizes ranging from about 1.0 mm to about 5.0 mm or more may be allowed. The pores could be differentially placed such that fill material may be preferentially extruded from certain zones of the container.

The container need not be woven and may be molded or otherwise formed as is known in the art. The preferred material may provide the ability to tailor bioabsorbance rates, for example, such as is disclosed in co-pending application Ser. No. 11/901,237, the disclosure of which is incorporated by reference herein in its entirety. Any suture-type material used medically may be used to form the container. The bag may be formed of plastic or even metal.

In at least one embodiment, container may be formed using a combination of resorbable and/or nonresorbable thread. The container may be partially or totally absorbable, metal, plastic, woven, solid, film, an extruded balloon or any other biocompatible material.

The container may be radio-opaque or include markings for x-ray visualization during insertion and filling. In an embodiment, such marking may include pad printing or other marking method with any biocompatible ink. According to one aspect, such medical grade biocompatible radiopaque ink may be loaded with tantalum powder. Marking may be placed at any desired location. In a preferred embodiment, markings may be placed at the proximal and distal ends of the container.

The fill material used in the present invention may include one or more of the following, or any other biocompatible material judged to have the desired physiologic response: Demineralized bone material, morselized bone graft, cortical, cancellous, or cortico-cancellous, including autograft, allograft, or xenograft; Any bone graft substitute or combination of bone graft substitutes, or combinations of bone graft and bone graft substitutes, or bone inducing substances, including but not limited to: calcium phosphates, calcium sulfates, calcium carbonates, hydroxyapatite, bone morphogenic proteins, calcified and/or decalcified bone derivatives; and Bone cements, such as injectable ceramic and polymethylmethacrylate bone cements.

One method of performing a percutaneous interbody fusion according to the present invention may include a combination of the following steps:

Positioning and neural monitoring to determine trajectory for surgical access which may include: Using anterior-posterior imaging, the surgeon may orient the guide pin on the skin, such that the tip is aligned with a line encompassing the lateral margins of the ipsilateral pedicles and centered on the disc. The surgeon may then mark the spot with a skin marker. Next the surgeon may re-orient the guide pin such that the tip is in a like spot on the contralateral side (lateral margin of the pedicles centered on the disc) and mark. A line may then be drawn that connects the dots and extends well lateral of each mark. This line indicates the implantation trajectory.

Next the surgeon may measure the width of the spine, the distance between the dots, and transpose this dimension laterally along the line in both directions from the lateral boarders of the spine. These locations may then be marked. These second set of marks indicate the approximate incision locations. The distance the incision is made from midline is largely dependent on patient size and the level of the pathology. The larger the patient and/or the lower the level, the further from midline the incision may need to be. (ex. at L4-5 in a heavy patient the incision location may need to be an additional 50% further lateral). The skin may then be incised at one of these marked incision locations.

The initial trajectory may be identified through the use of active EMG neural stimulation. To prepare the equipment for probing the exchange tube may be placed over the neural stimulating component until the exchange tube contacts the handle. A return lead needle may then be placed through the patient's skin and into the posterior musculature approximately 5-8 cm, or the desired depth from the incision site. The EMG machine may then be set to deliver approximately 10 mA, or the desired amperage to the neural stimulating component.

The surgeon may use image guidance to insert and advance the neural stimulating component as desired while targeting the superior lateral wall of the pedicle immediately inferior to the target disc. This will prevent inadvertent transgression of the foramen and canal and aid in guiding the tip of the neural stimulating component to a position medial to the exiting root. As the neural stimulating component is advanced, as is shown in FIG. 2, the electrified tip will be seeking to evoke a neural response. If at any time the technician detects a response, the physician will cease advancement and may slightly retract the neural stimulating component because the response is an indication that the nerve root is in, or near, the current trajectory. At this point one of two actions may be taken: either the power is titrated down to the desired amperage or the neural stimulating component is redirected to a slightly more inferior and/or medial orientation. The physician may then commence re-advancement of the neural stimulating component.

Initial bony contact should be with the pedicle. When contact is made, the tip of the neural stimulating component should appear to be on the superior lateral wall of the pedicle immediately inferior to the target disc.

The surgeon may then use lateral imaging to inspect the location of the neural stimulating component tip. The objective is to place the tip at the superior edge of pedicle slightly posterior to the pedicle-vertebral body junction. If it is not at this location, the surgeon may retract the neural stimulating component, alter the insertion angle, and/or re-advance the neural stimulating component until it is. The surgeon may next re-orient the C-arm for AP imaging and inspect the neural stimulating component tip position. If the tip appears at the base of the pedicle on the lateral projection and the lateral edge of the pedicle in the AP projection the tip is in the correct location to proceed.

Next, the surgeon may slide the neural monitoring tip superiorly and medially along the base of the pedicle until it appears to be on the disc immediately superior to the pedicle, approximately equidistant between the medial and lateral margins of the pedicle and near the inferior endplate of the target disc. The exiting nerve root occupies the superior most portion of the foramen making placement into the disc in a position as inferior as possible desirable for patient safety. It is not a requirement that the neural stimulating component be centered on the disc as subsequent dilation instruments will center the subsequent instruments and gently move the exiting root superiorly as the space is distracted. During this maneuver, if a neural response is evoked, the surgeon may determine which nerve root has responded. If it is the exiting root the neural monitoring neural stimulating component is likely too superior or lateral within the foramen, if it is the traversing root (root exiting at the level below) the placement may be too medial. Once this response has been determined the neural stimulating component may be slightly retracted and/or repositioned farther away from the offended nerve root.

If a location cannot be identified in which a neural response is not evoked at 5 mA or the desired amperage, it may be indicative of a highly compressed foramen in which the neural elements are filling a significant portion of the foraminal volume. Should this happen, the amperage may again be turned down slightly (for example, to 4 mA) and the neural stimulating component may be re-advanced very slowly in order to determine if a response is evoked. This process of retracting the neural stimulating component and slowly re-advancing may be repeated until no response is evoked.

Once a "no response" level is established at the target location the neural stimulating component may once again be withdrawn, but prior to re-advancement the power setting is not altered and the neural stimulating component is reoriented so that re-advancement will place the neural stimulating component tip more superiorly in the foramen. Upon readvancement, an evoked response indicates that the power setting is sufficient to penetrate the neural sheath, evoke a response, and thus provide navigation past the nerve root. After this positive reaction is evoked the surgeon may revert back to the previous trajectory and re-navigate to the level of the disc.

If no response is again seen in this more superior position it is an indication that either the nerve sheath cannot be penetrated with the low power setting or the nerve root is filling the entire foramen. In either instance EMG guidance is not sensitive enough to identify a navigable trajectory past the nerve. In this instance the procedure may be reattempted from the contralateral side or aborted.

Once the neural stimulating component tip is observed to be on the disc, the energy may be turned to zero and the exchange tube may be slid down the neural stimulating component shaft to the disc. Slight pressure may be used to hold the tip against the disc. The neural stimulating component may then be removed from the exchange tube and may be replaced with a pointed guide pin.

The surgeon may now revert back to AP imaging and may advance the guide pin until the pin tip is observed to be nearing the lateral margin of the canal (medial borders of the pedicles). Then, the surgeon may revert again to lateral imaging. If the guide pin tip is now seen to be anterior to the posterior margin of the disc, the surgeon may continue to use lateral imaging and may advance the guide pin into the disc until the pin tip appears to be at the midpoint. The surgeon may re-orient the C-arm to AP and image. If the trajectory is correct, the guide pin tip will appear to be in the midline on the AP image. If the trajectory is too flat (pin tip across midline) or too steep (pin tip not yet to midline), the guide pin trajectory may be adjusted accordingly. Failure to achieve the correct trajectory may result in container and bone graft placement that is either anterior and lateral (angle too steep) or posterior and lateral (angle too flat).

Figure 3:
FIG. 3 depicts one embodiment of a first dilator.

Sequential Dilation: Once the correct pin trajectory is determined, the exchange tube may be removed. Using lateral imagery, the surgeon may pass, for example a 4.0 mm, or other desired size, first sequential dilator over the guide pin, as is depicted in FIG. 3. Imaging may be taken frequently to ensure the guide pin does not advance. An impaction cap may be placed over the end of the guide pin and placed against the back end of the about 4.0 mm sequential dilator. The first sequential dilator may be impacted approximately 25% of the way across the spine. The guide pin may then be removed.

Figure 4:
FIG. 4 depicts an embodiment of a second dilator.

A second sequential dilator, about 6.5 mm or other desired size, may then be placed over the first sequential dilator, as is shown in FIG. 4. The second sequential dilator may be advanced toward the spine. Imaging may be taken frequently to ensure the first sequential dilator does not advance. An impaction cap may then be placed over the end of the first sequential dilator and placed against the proximal end of second sequential dilator. The second sequential dilator may be impacted until the distal end of the dilator is approximately 25% of the way across the disc space. Remove the first sequential dilator. Additional dilators may be advanced in the same manner as needed.

Figure 5:
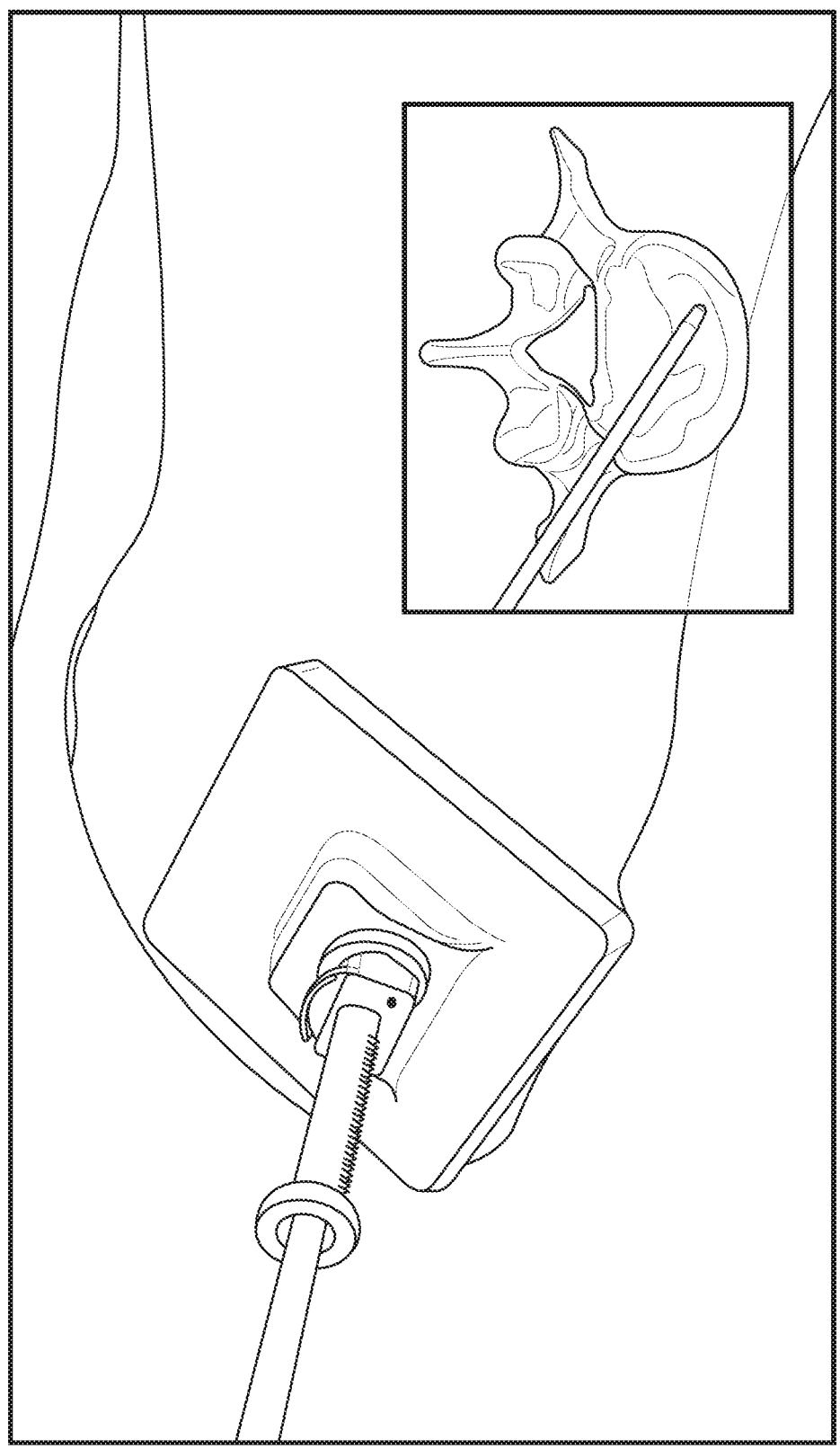
FIG. 5 illustrates an embodiment of a force dissipation apparatus.

Instrument Alignment: In an embodiment, a force dissipation and instrument alignment device, illustrated in FIG. 5, as disclosed in co-pending application Ser. No. 11/655,730, the contents of which are incorporated herein in their entirety, may be used. If such a device is used, the steps may be as follows: the alignment device may be placed over the dilator until the base of the alignment device contacts the patient. The portal sleeve of the alignment device will extend into the incision. An access portal may then be placed over the dilator and through the portal sleeve. The surgeon may use lateral imaging to advance the access portal until the access portal tip abuts the disc.

Figure 6:
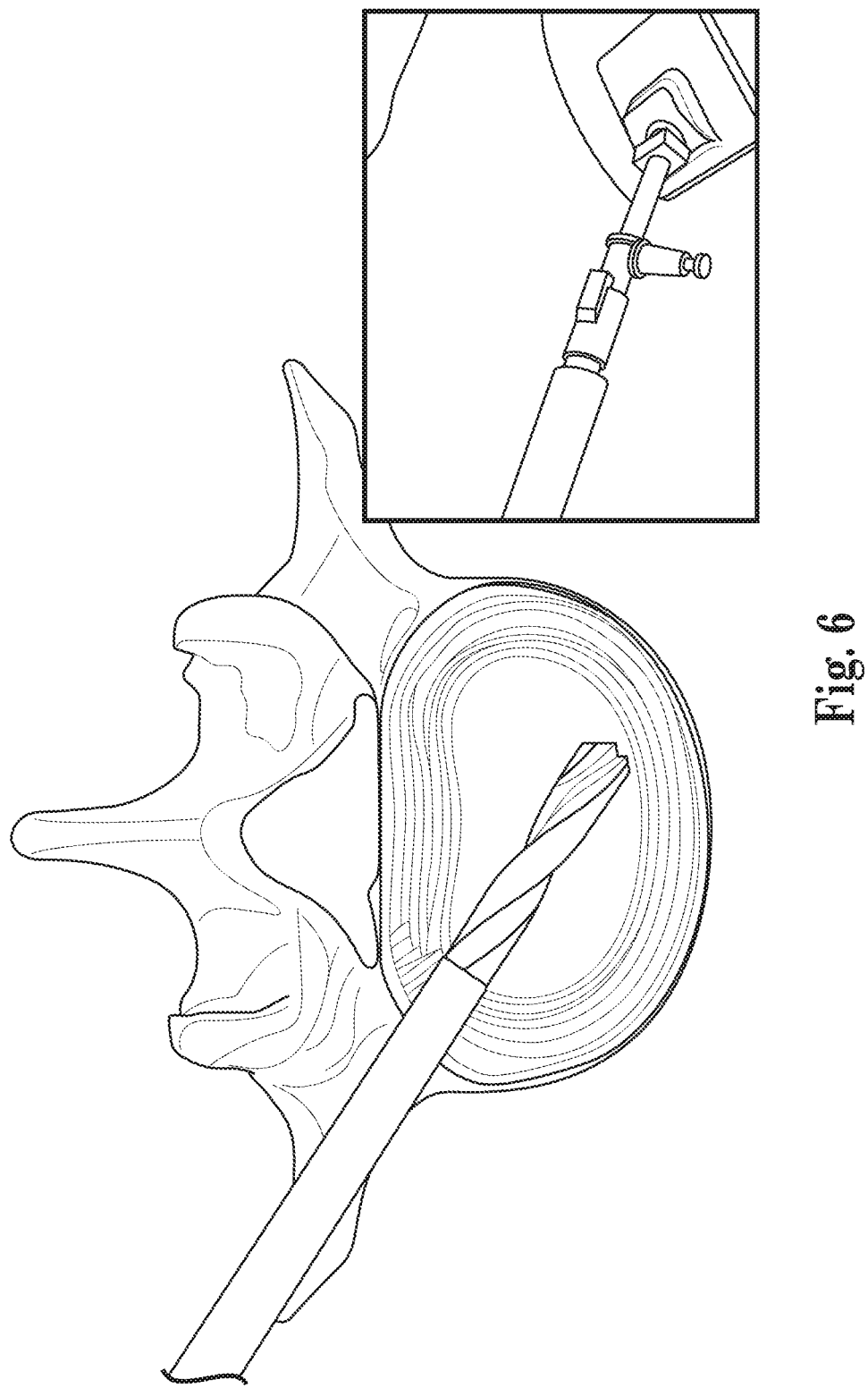
FIG. 6 illustrates an embodiment of a screw placed through an embodiment of an access portal.

An impactor may be placed over the dilator and tapped with a mallet until the access portal tip advances approximately 5 mm, or the desired depth into the disc. The dilator may then be removed. As shown in FIG. 6, a drill may then be passed through the access portal. The surgeon may begin drilling and may monitor the progress with lateral imagery. The drill may be advanced until contact is made with the positive stop of the access portal or the tip of the drill appears to traverse approximately ¾ of the way across the disc or to the desired depth. When the desired depth is achieved, the final drilling depth can be read immediately below the positive stop collar on the access portal. The surgeon may make note of this depth to assist in selecting a container size. The drill may then be removed.

Figure 7:
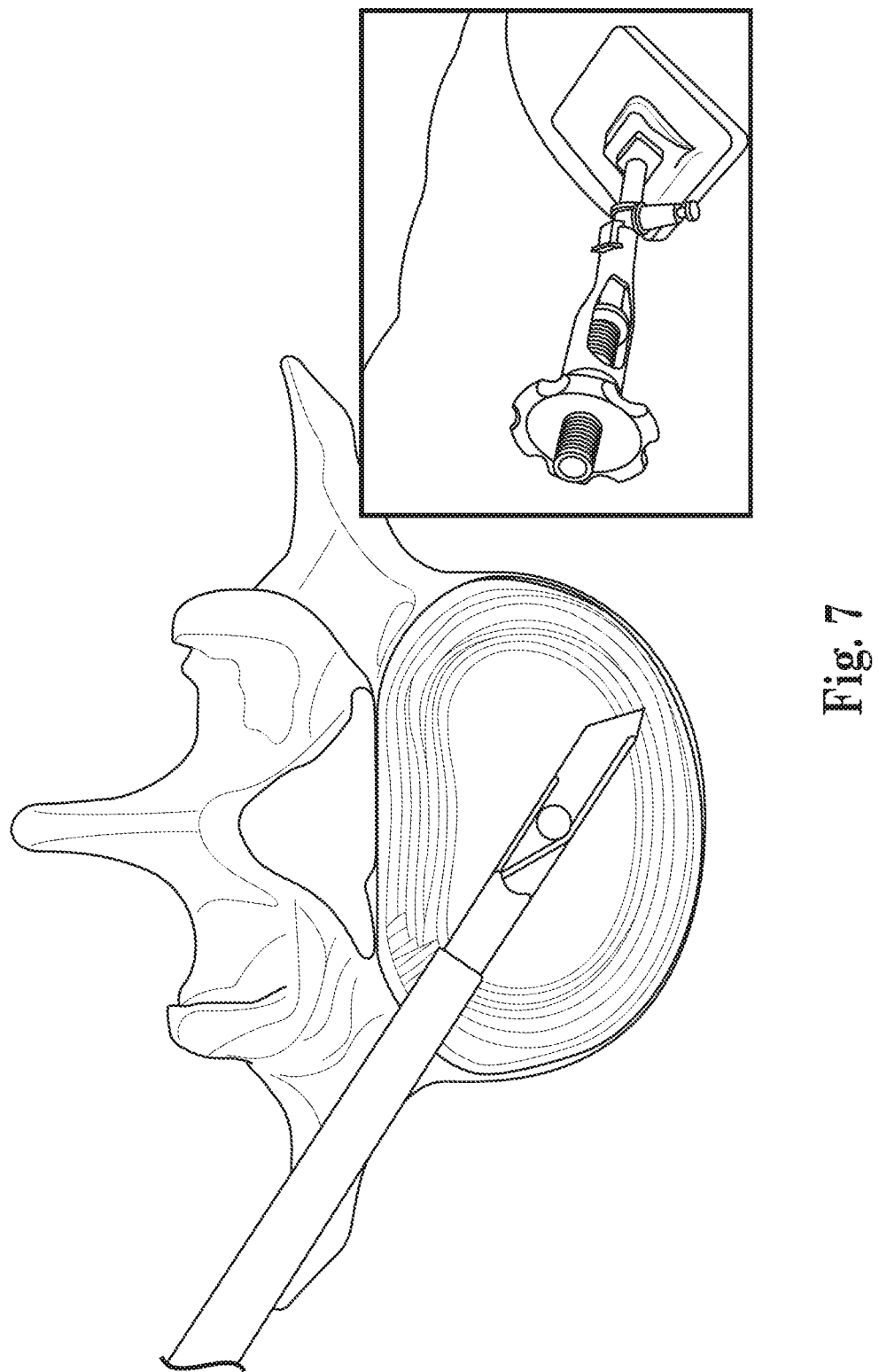
FIG. 7 depicts an embodiment of a shaper in a collapsed position.
Figure 8:
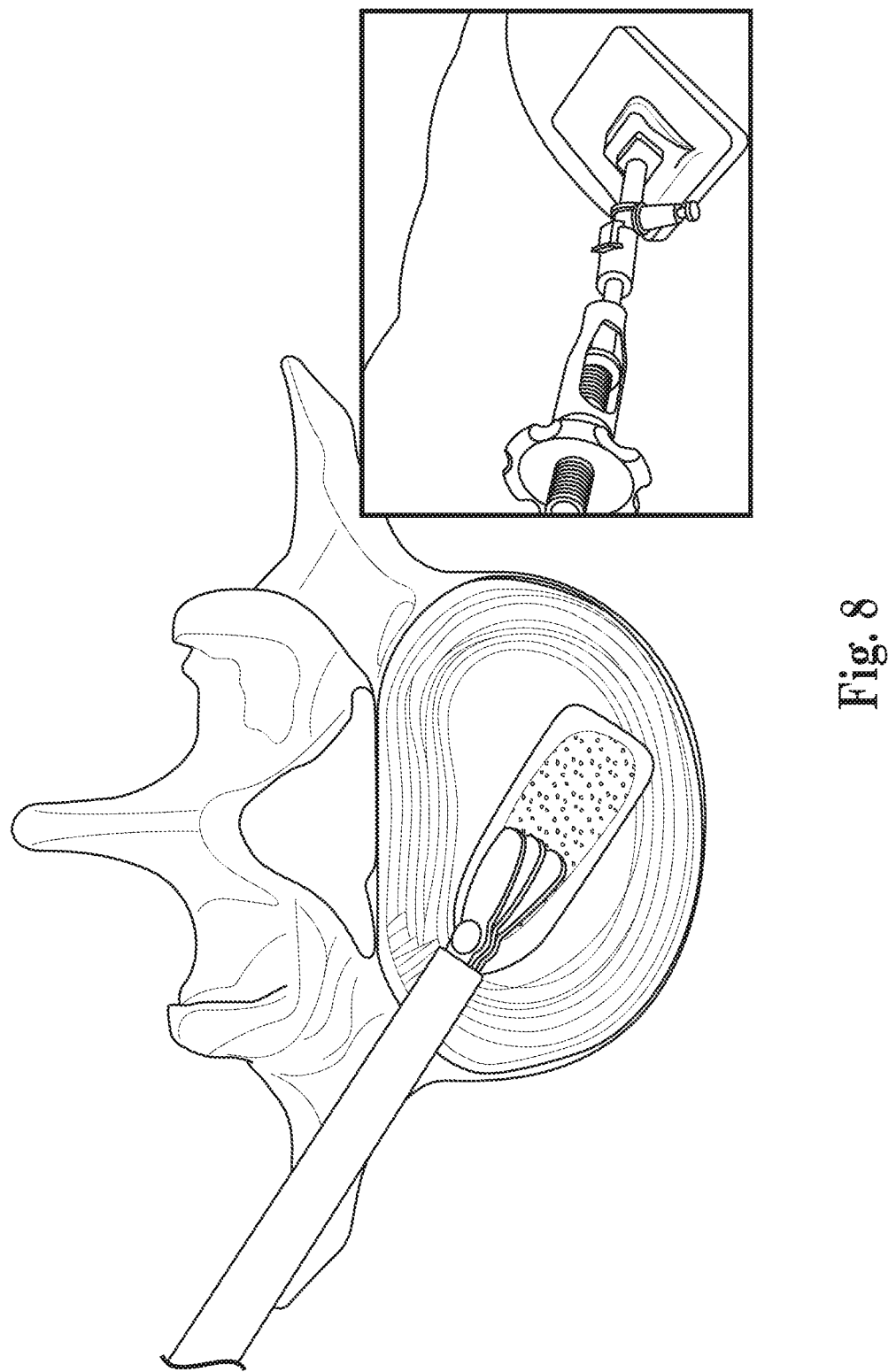
FIG. 8 depicts an embodiment of a shaper in an expanded position.
Figure 9:
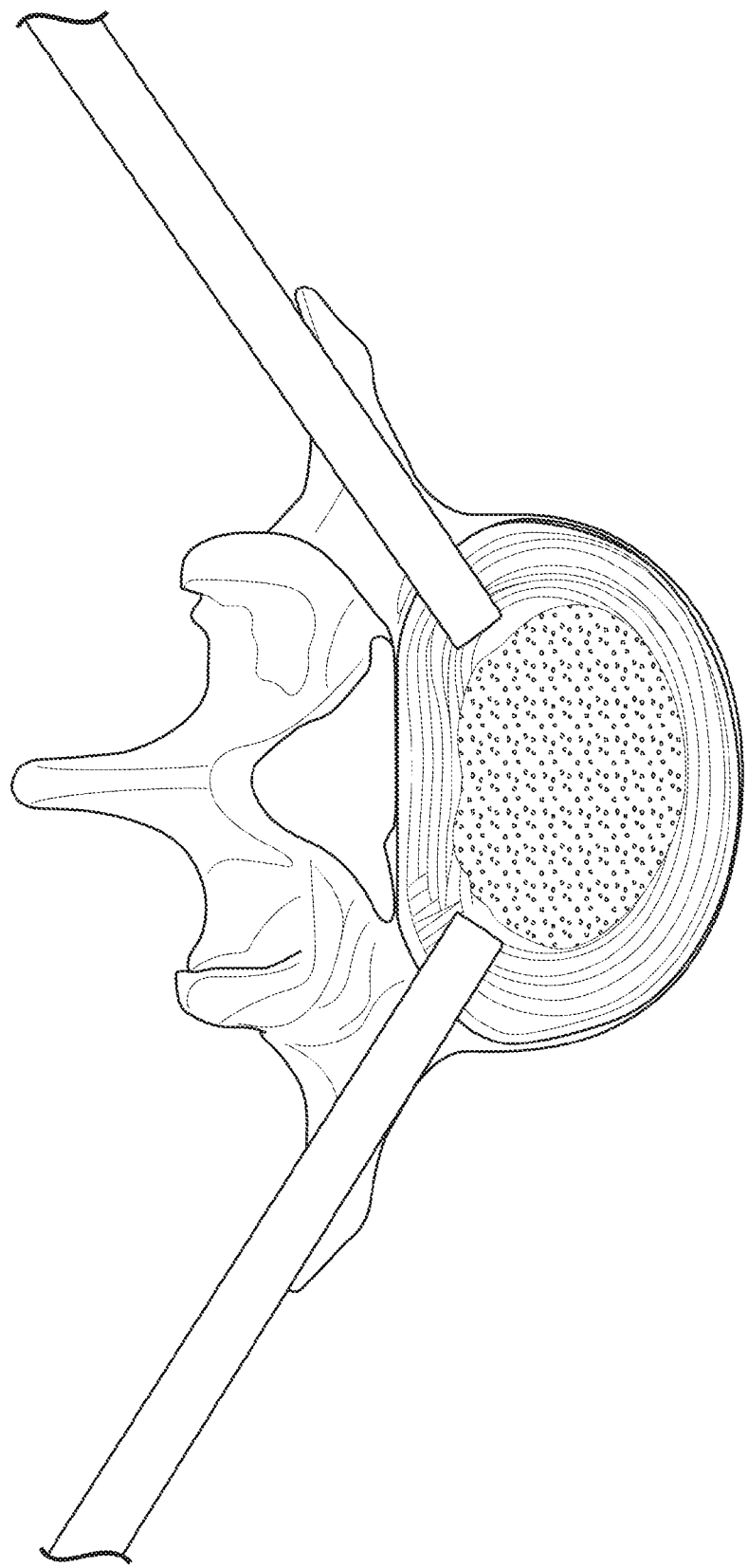
FIG. 9 illustrates an embodiment of a reamed out intervertebral cavity after the use of a shaper.
Figure 10:
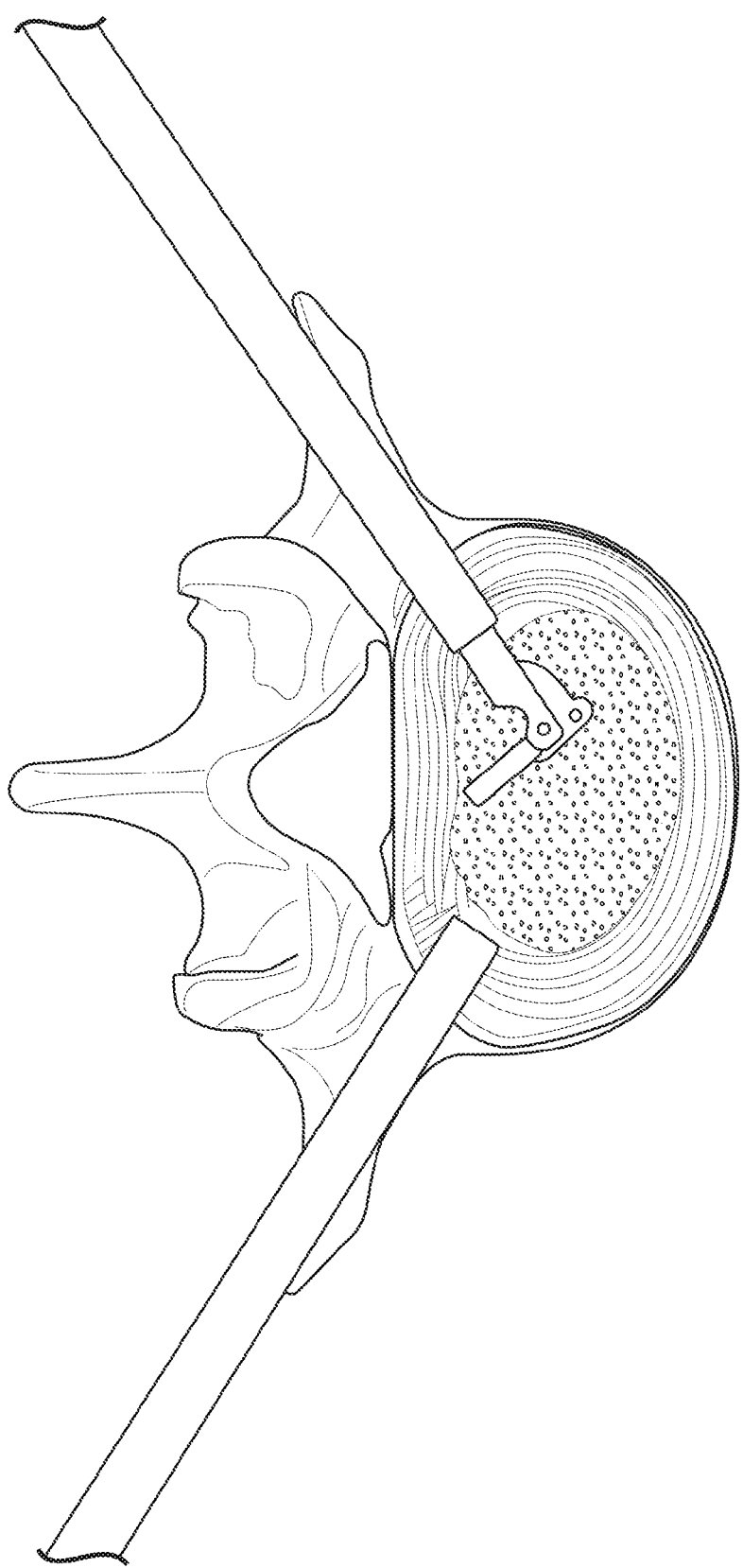
FIG. 10 depicts an embodiment of a tissue removal tool.
Figure 11:
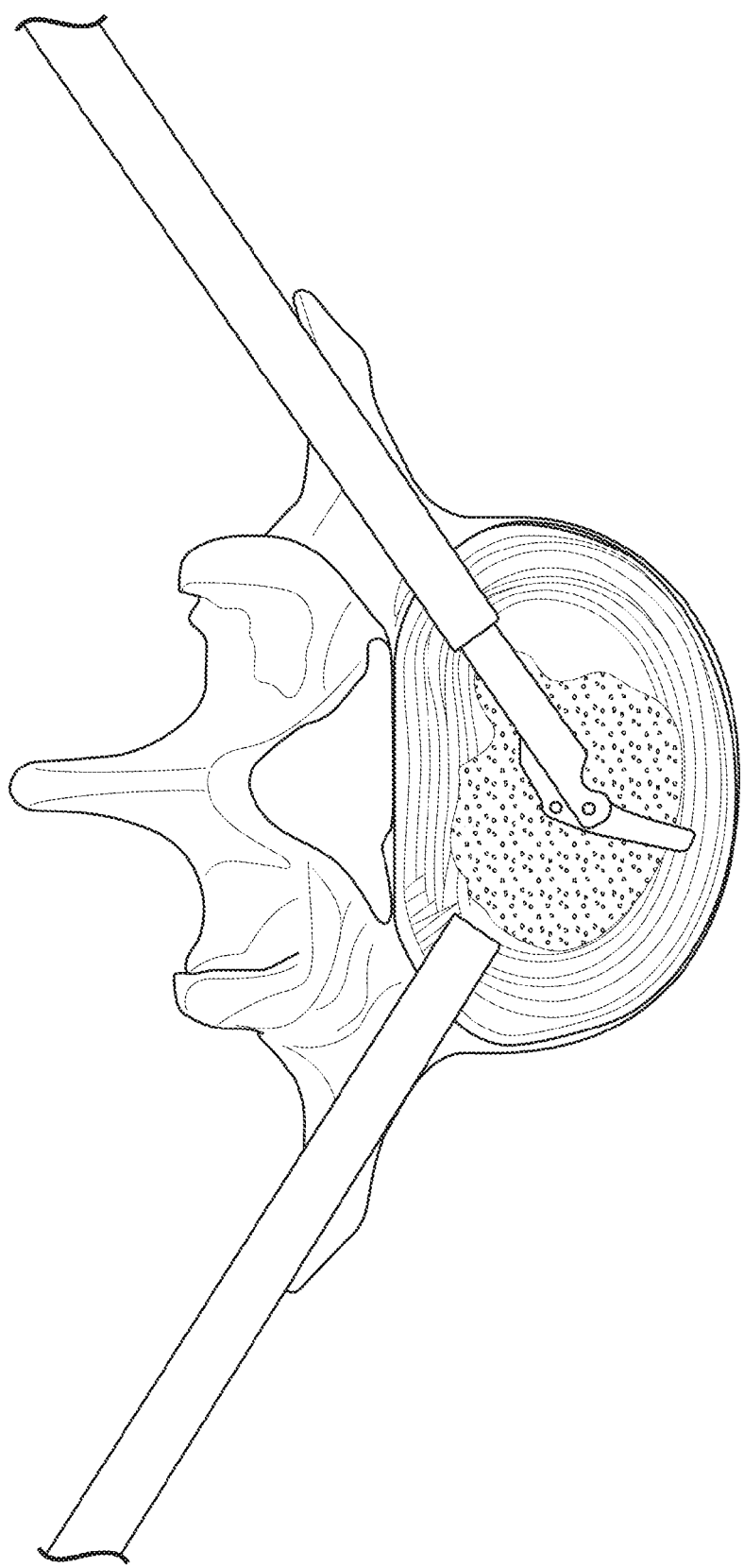
FIG. 11 illustrates a bilateral embodiment of the present invention wherein a second tissue removal tool is used.
Figure 12:
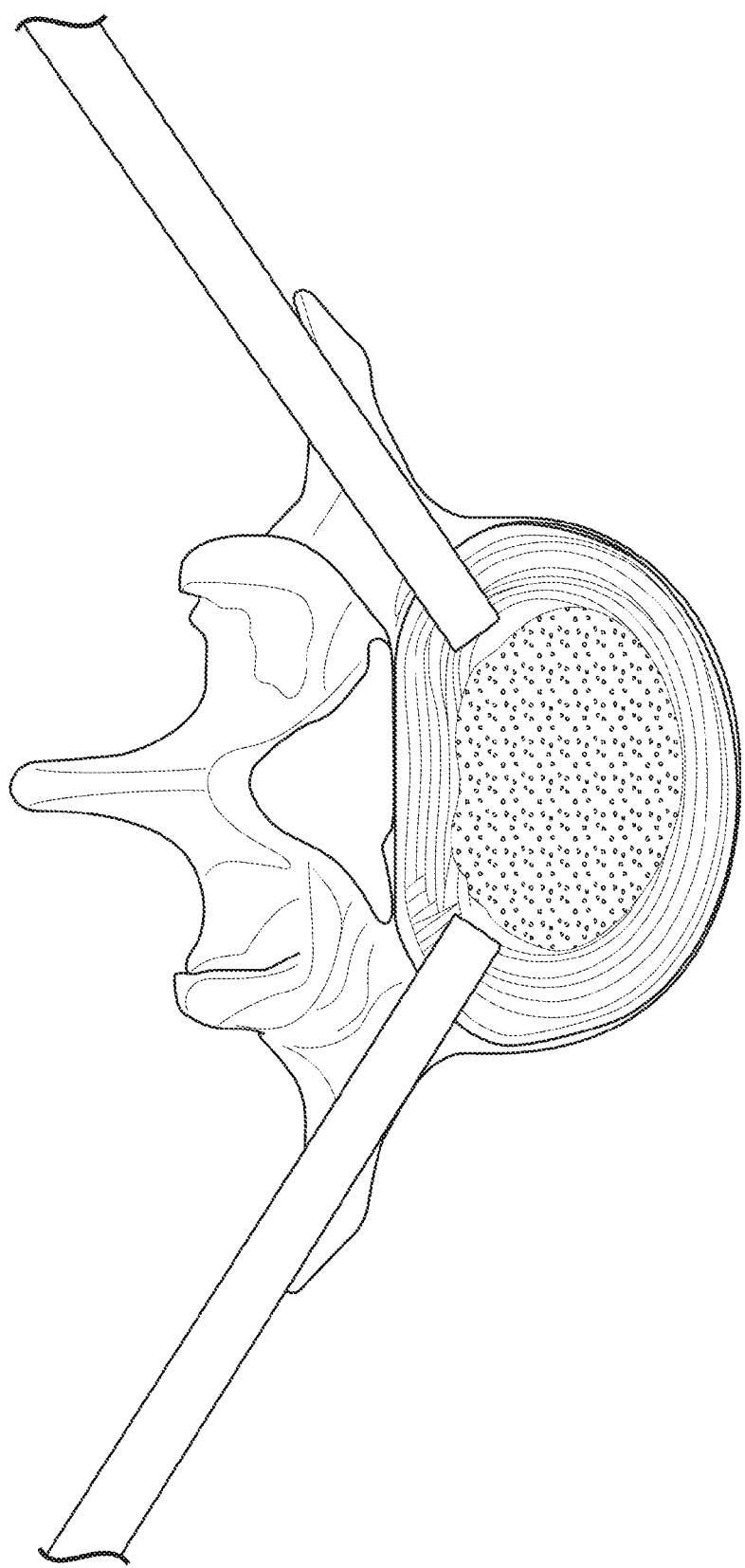
FIG. 12 depicts an embodiment of a cleared intervertebral cavity.

Discectomy and Cavity Creation: A shaper, an example of which is shown in FIGS. 7, 8 and 9 may be used to facilitate discectomy and decortication of the central portion of the disc space. A shaper may be passed through the access portal until the shaper body contacts the access portal positive stop. Shaping may be observed with lateral or oblique imagery to monitor access portal tip location, depth of instrument insertion and amount of decortication. The surgeon may then remove the disc and endplate using the desired tool and method, an example of which is shown in FIGS. 10, 11 and 12 until the desired decortication is reached.

Figure 13:
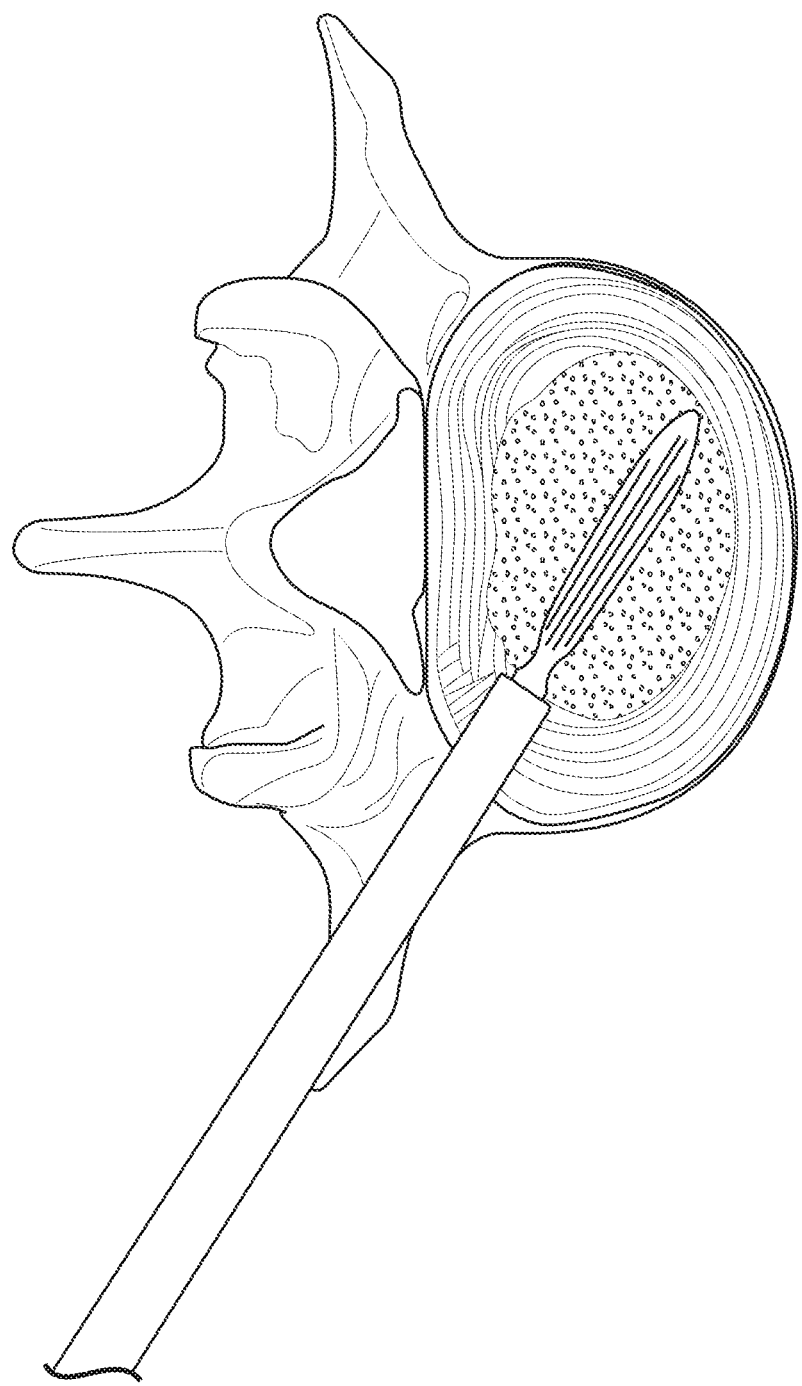
FIG. 13 illustrates an embodiment of a discectomy evaluation device in a collapsed state.
Figure 14:
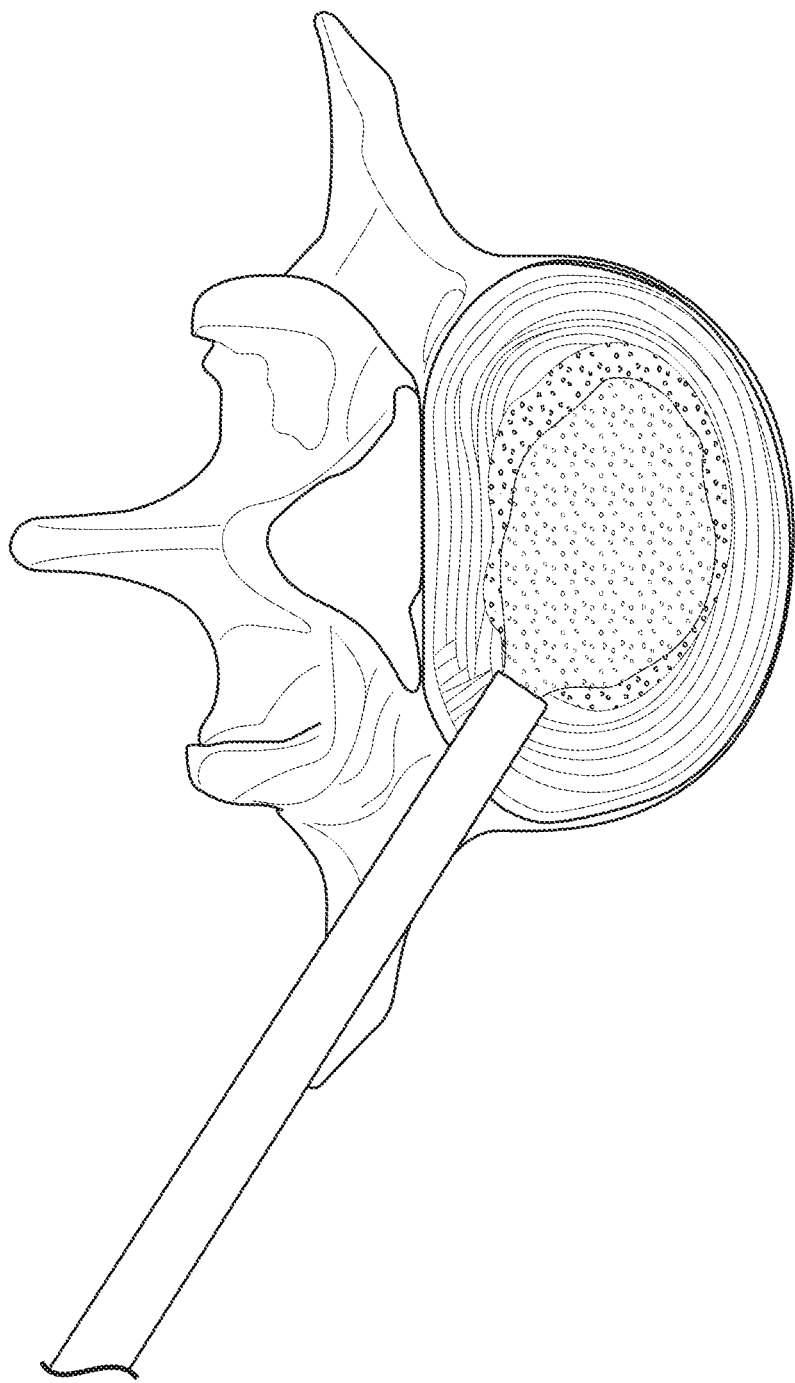
FIG. 14 illustrates an embodiment of a discectomy evaluation device in an inflated state.

To validate that the disc has been removed and appropriate decortication has been done a discectomy validation device may be used. As is shown in FIG. 13, the discectomy validation device may be passed through an access portal and into the disc space to the distal end of the cavity. The discectomy validation device may then be filled with a contrast solution or other fluid using low pressure as shown in FIG. 14. High pressure filling is undesirable as it may result in disc herniation. A series of AP, lateral, and oblique images may be taken to evaluate the thoroughness of the disc removal and endplate decortication. If unwanted disc and endplate material is remaining discectomy validation device will outline their location within the disc space. The discectomy validation device may then be deflated and removed. If necessary the additional disc and endplate material may be removed and the disc space may be reinspected by placing the discectomy validation device a second time. This validation may be repeated as desired.

Figure 15:
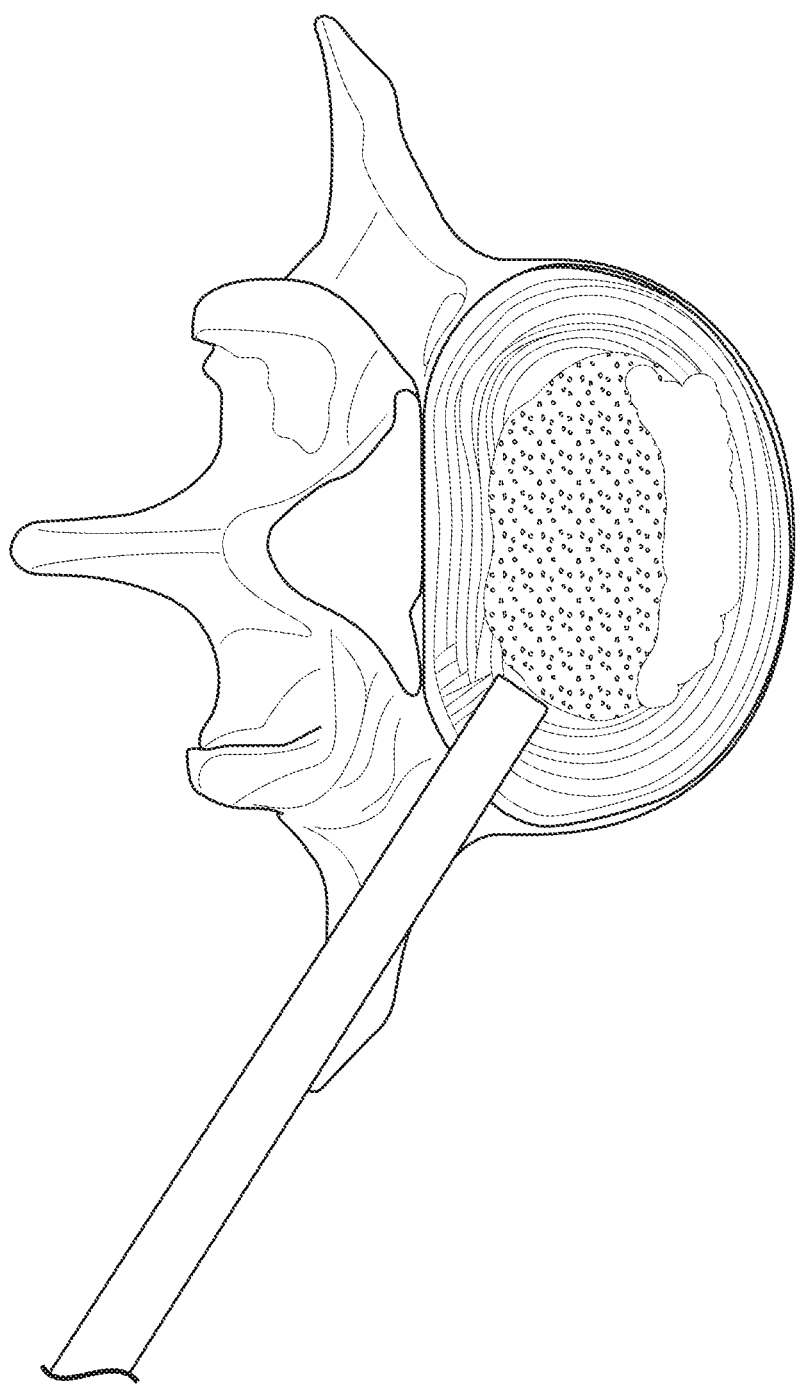
FIG. 15 depicts the placement of sentinel graft.

Container selection and Placement: The surgeon determines the appropriate container size. Such determination may be based on the drilling depth and the anticipated final disc height. The discectomy evaluation device may also be used to approximate the desired size of the container. The surgeon may fill the bladder portion of the discectomy evaluation device to the desired size and shape and use the amount of solution used to determine the desired container size. Should the surgeon desire to use sentinel graft (i.e., uncontained bone graft used as a post-operative radiographic assessment guide), the surgeon may place the sentinel graft, as shown in FIG. 15, directly into the access portal and use the back end of the dilator to pack the graft into the anterior portion of the disc, or the surgeon may place a full fill tube into a sentinel grafting spacer and tamp bone out of the tube with a push rod and mallet.

Once the sentinel graft is placed, the dilator may be advanced through the access portal until it contacts the annulus to displace the sentinel graft to the lateral recesses of the disc space and limit any interference the sentinel graft may have with container deployment.

Figure 16:
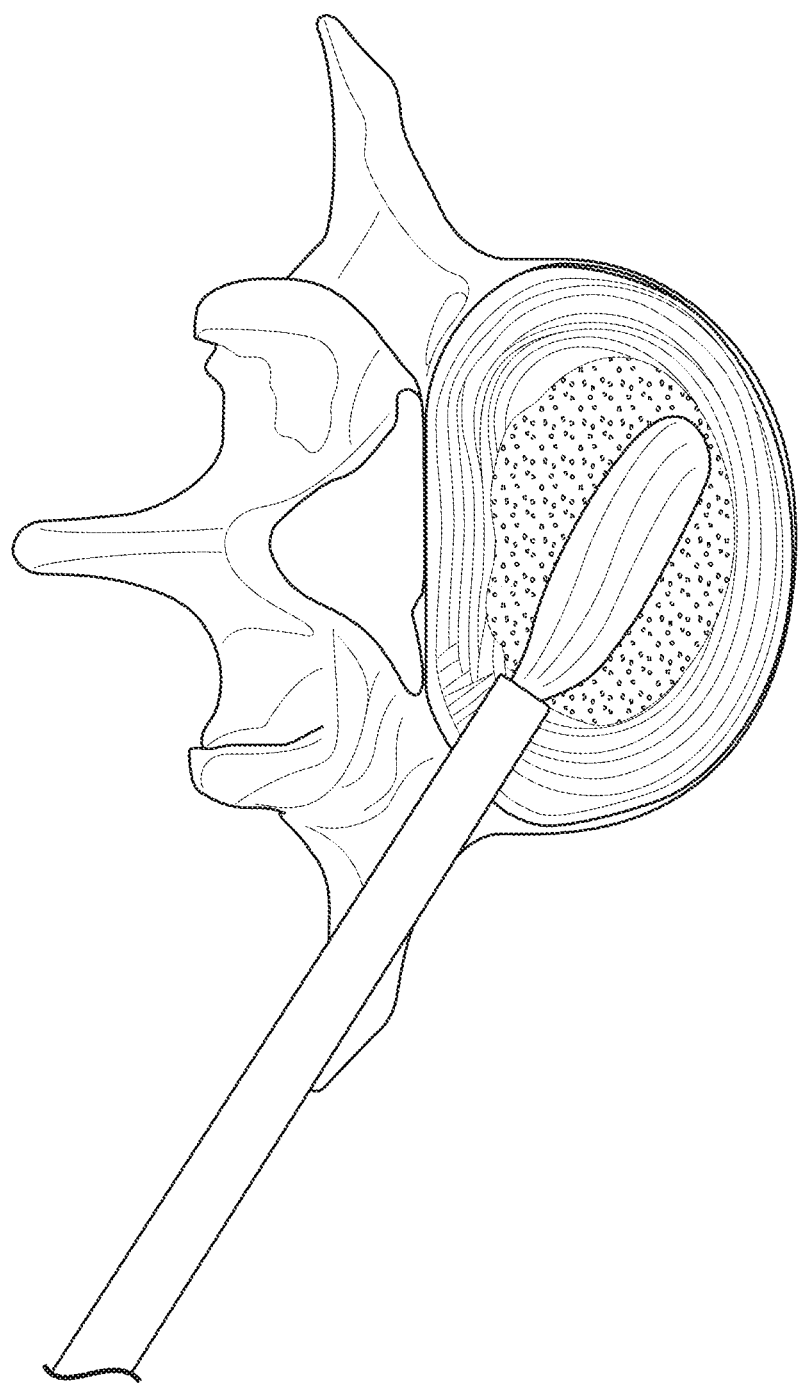
FIG. 16 illustrates an embodiment of a container in a collapsed state according to the present invention.

One method of container insertion may include the steps of: assembling the container to a container holder by rotating a thumbwheel on the container holder to move a lock tube stop to a proximal position; Aligning an arrow on the container holder with a notch on a metal tip of the container and notches in the container holder with a shoulder of the metal tip; Pressing the container into the container holder; Spinning a thumbwheel clockwise until a stop abuts with a lock tube; Passing a container extender through a cannulation in the container holder; Extending the container; Advancing the container through the access portal by pressing simultaneously on the container extender and the container holder, as is shown in FIG. 16; Ensuring the container is well deployed and removing the container holder. Other methods of deploying the mesh may be used and are within the scope of this disclosure.

Figure 17:
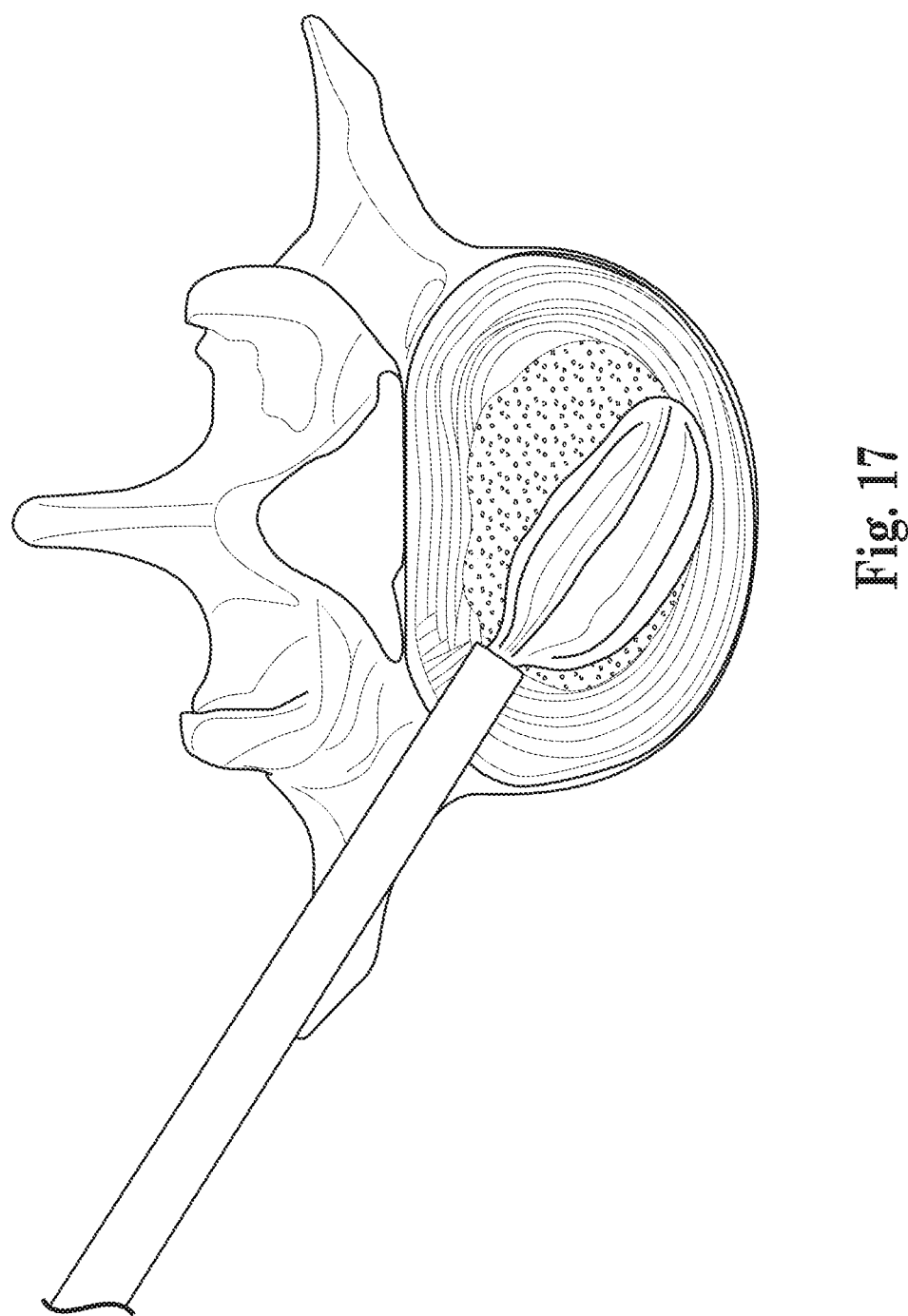
FIG. 17 illustrates an embodiment of a container according to the present invention in a partially filled state.
Figure 18:
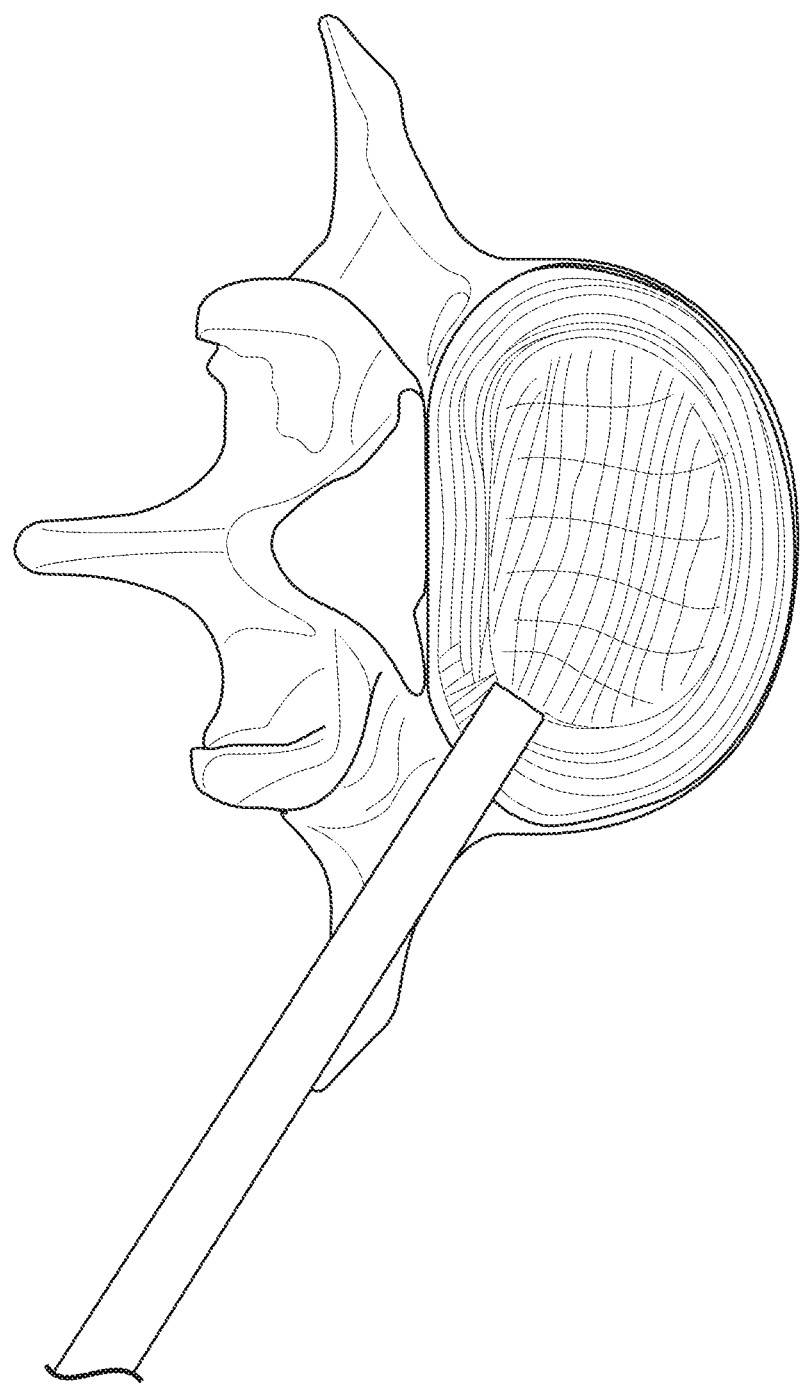
FIG. 18 illustrates an embodiment of a container according to the present invention in a filled state.
Figure 19:
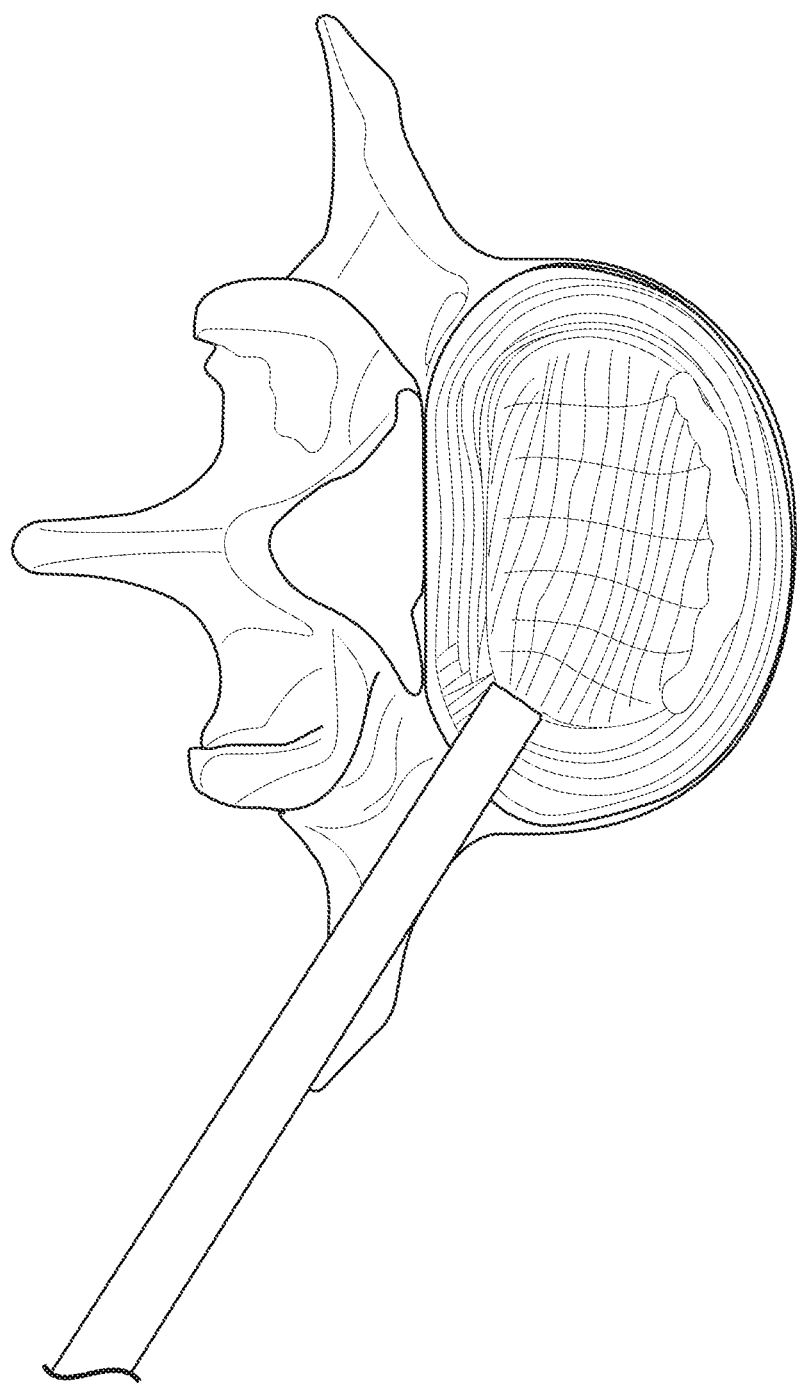
FIG. 19 illustrated an embodiment an intervertebral cavity after container and sentinel graft placement.

Filling the Container: The amount of fill material required to fill a container may be determined by the container size and desired final shape. Fill materials and tools for inserting the fill materials according to some embodiments of the present invention have been disclosed in the following patents and co-pending U.S. Pat. Nos. 6,620,169, 6,620,162, 7,025,771 and Ser. No. 10/924,240, the disclosures of which are incorporated in the entirety herein. Once the container is filled to the desired fill capacity as is shown in FIGS. 17, 18 and 19, the access portal and instrument alignment device may be removed and the incisions may be sutured.

The surgeon may then choose to place screws for added support and stabilization as is shown in FIG. 20.

The above-described steps are an example of one method of performing a percutaneous fusion according to the present invention. The steps may be completed in a different order, some steps may be omitted or other steps may be added at the physician's discretion.

What is claimed is:

1. A method of performing percutaneous interbody spinal fusion on adjacent vertebrae of a patient, the method comprising:
   creating a percutaneous access opening into the patient;
   using indirect visualization, without retraction,
      to establish a surgical path to an intervertebral disc through the percutaneous access opening;
   after establishing the surgical path to the intervertebral disc through the percutaneous access opening, creating a cavity in the intervertebral disc by inserting an instrument through the surgical path, without retraction of the percutaneous access opening;
   inserting an implantable device into the created cavity through the surgical path in an undeployed state, wherein the implantable device in the undeployed state is sized to fit through the percutaneous access opening without retraction of the percutaneous access opening; and
   after inserting the implantable device into the cavity, filling the implantable device with fill material through the surgical path via the percutaneous access opening.

2. The method of claim 1, further comprising the step of sequential dilation of the surgical path prior to the step of creating the cavity in the intervertebral disc space.

3. The method of claim 1, further comprising the step of filling the device sufficiently to distract the adjacent vertebrae.

4. The method of claim 1, wherein all instrumentation for accessing the intervertebral disc space is introduced through the same surgical path.

5. The method of claim 1 further including sequentially dilating the surgical path prior to forming the cavity in the disc, comprising the steps of:
inserting a first dilator through the surgical path, the first dilator including a tapered tip, wherein the first dilator is inserted until the tapered tip penetrates into the vertebral disc to deflect neural structures outward to a major diameter of the first dilator;
inserting a second dilator through the surgical path and over the first dilator, the second dilator having a larger outer diameter than the first dilator, the second dilator including having a tapered tip configured to further deflect the neural structures outward to a major diameter of the second dilator.

6. The method of claim 1, further comprising evaluating the cavity created in the intervertebral disc, including inserting a discectomy evaluation device through the percutaneous surgical path.

7. A method for performing percutaneous interbody spinal fusion on adjacent vertebrae of a patient, the method comprising:
providing imaging equipment adapted to provide indirect visualization of the patient during the percutaneous interbody spinal fusion procedure and present images of the patient's internal anatomy on a viewing screen visible to a surgeon performing the percutaneous interbody spinal fusion procedure;
forming a percutaneous surgical path to an intervertebral disc between the adjacent vertebrae;
inserting at least one disc cavity creation tool through the percutaneous surgical path;
creating the cavity in an intervertebral disc space of the adjacent vertebrae with the at least one disc cavity creation tool;
inserting through the percutaneous surgical path an expandable implant in an undeployed state;
filling the collapsed expandable implant through the percutaneous surgical path with fill material to expand the expandable implant within the cavity in the intervertebral disc space; and
providing instructions for use of the expandable implant to perform the percutaneous interbody spinal fusion procedure.

8. The method of claim 7, further comprising the step of inserting sequential dilators through the percutaneous surgical path.

9. The method of claim 7, further comprising providing markings to the implant for x-ray visualization.

10. The method of claim 7, further comprising sequentially dilating the percutaneous surgical path prior to forming the cavity in the disc, comprising the steps of:
inserting a first dilator through the percutaneous surgical path, the first dilator including a tapered tip, wherein the first dilator is inserted until the tapered tip penetrates into the intervertebral disc to deflect neural structures outward to a major diameter of the first dilator; and
inserting a second dilator through the percutaneous surgical path and over the first dilator, the second dilator having a larger outer diameter than the first dilator, the second dilator including a tapered tip configured to further deflect the neural structures outward to a major diameter of the second dilator.

11. The method of claim 7, further comprising filling the expandable implant through the percutaneous surgical path sufficiently to distract the adjacent vertebrae.

12. The method of claim 7, further comprising evaluating the cavity created in the intervertebral disc, including inserting a discectomy evaluation device through the percutaneous surgical path.

13. A method of performing percutaneous interbody spinal fusion on adjacent vertebrae of a patient, the method comprising:
creating a percutaneous access opening in the patient;
establishing a percutaneous surgical path through the percutaneous access opening, without retraction of the percutaneous access opening and without directly viewing the surgical path, to a vertebral disc of the patient between the adjacent vertebrae to be fused;
inserting at least one disc cavity creation tool through the percutaneous surgical path and creating a cavity in an intervertebral disc space of the adjacent vertebrae;
after the cavity is created in the intervertebral disc space, inserting an expandable device sized and configured to fit through the access opening, without retraction of the percutaneous surgical path, into the cavity; and
filling the expandable device, after insertion into the cavity, with fill material via the surgical path.

14. The method of claim 13, wherein all instrumentation for accessing the intervertebral disc space is introduced through the same percutaneous surgical path.

15. The method of claim 13, further comprising providing markings to the device for x-ray visualization.

16. The method of claim 13, further comprising the step of sequential dilation of the percutaneous surgical path prior to forming the cavity in the intervertebral disc space, the sequential dilation step comprising:
inserting a first dilator through the percutaneous surgical path, the first dilator including a tapered tip, wherein the first dilator is inserted until the tapered tip penetrates into the vertebral disc to deflect neural structures outward to a major diameter of the first dilator; and
inserting a second dilator through the percutaneous surgical path and over the first dilator, the second dilator having a larger outer diameter than the first dilator, the second dilator including having a tapered tip configured to further deflect the neural structures outward to a major diameter of the second dilator.

17. The method of claim 13, further including the step of filling the expandable device through the percutaneous surgical path sufficiently to distract the adjacent vertebrae.

18. The method of claim 13, further comprising providing imaging equipment adapted to provide indirect visualization of the patient during the percutaneous interbody spinal fusion procedure and present images of the patient's internal anatomy on a viewing screen visible to a surgeon performing the percutaneous interbody spinal fusion procedure.

19. The method of claim 13, wherein the step of establishing a surgical path through the percutaneous access opening includes using indirect visualization, without retraction, to place a neural monitoring probe into the percutaneous access opening to establish the surgical path to an intervertebral disc via neural monitoring.

20. The method of claim 13, further comprising the step of evaluating the cavity created in the intervertebral disc space, including inserting a discectomy evaluation device through the percutaneous surgical path.

* * * * *